(12) United States Patent  
Cerruti et al.

(10) Patent No.: US 10,407,556 B2  
(45) Date of Patent: Sep. 10, 2019

(54) SURFACE MODIFICATION METHODS FOR BIOMEDICAL SCAFFOLDS

(71) Applicant: THE ROYAL INSTITUTION FOR THE ADVANCEMENT OF LEARNING/MCGILL UNIVERSITY, Montreal (CA)

(72) Inventors: Marta Cerruti, Montreal (CA); Hesameddin Mahjoubi, Montreal (CA)

(73) Assignee: THE ROYAL INSTITUTION FOR THE ADVANCEMENT OF LEARNING/MCGILL UNIVERSITY, Montreal, QC (CA)

( * ) Notice: Subject to any disclaimer, the term of this patent is extended or adjusted under 35 U.S.C. 154(b) by 114 days.

(21) Appl. No.: 15/317,151

(22) PCT Filed: Jun. 11, 2015

(86) PCT No.: PCT/CA2015/000378  
§ 371 (c)(1),  
(2) Date: Dec. 8, 2016

(87) PCT Pub. No.: WO2015/188261  
PCT Pub. Date: Dec. 17, 2015

(65) Prior Publication Data  
US 2017/0137588 A1 May 18, 2017

Related U.S. Application Data

(60) Provisional application No. 62/010,630, filed on Jun. 11, 2014.

(51) Int. Cl.  
*C08J 7/12* (2006.01)  
*A61L 27/16* (2006.01)  
(Continued)

(52) U.S. Cl.  
CPC .............. *C08J 7/12* (2013.01); *A61L 27/16* (2013.01); *A61L 27/18* (2013.01); *A61L 27/50* (2013.01);  
(Continued)

(58) Field of Classification Search  
CPC .................................. C08J 7/12; A61L 27/50  
(Continued)

(56) References Cited

U.S. PATENT DOCUMENTS 6,555,175 B2 * 4/2003 Johnson ............... C08J 7/12  
427/393.5  
6,586,038 B1 * 7/2003 Chabrecek ............ C08J 7/12  
351/159.33  
(Continued)

FOREIGN PATENT DOCUMENTS

WO 2013/050554 4/2013

OTHER PUBLICATIONS

Le et al. Covalent Grafting of Chitosan onto Stainless Steel through Aryldiazonium Self-Adhesive Layers. Applied Materials and Interfaces, Vo.I. 6, pp. 9085-9092 (Year: 2014).*

(Continued)

*Primary Examiner* — Cachet I Proctor  
(74) *Attorney, Agent, or Firm* — Norton Rose Fulbright LLP

(57) ABSTRACT

Many different substrates are used in tissue engineering as platforms to enhance cell attachment, proliferation and activity, either in-vitro, to multiply specific cell lines, or in-vivo, to induce shorter healing time of injured or missing tissue. However, their hydrophobicity and lack of specific functionalities make them non-ideal for cell adhesion and growth. Treating the surfaces by exposing them to a series of steps including, but not limited to, a diazonium based wet chemistry allows one or more functional groups to be (Continued)

applied to the surface improving cell adhesion and growth. Embodiments of the invention exploiting PDLLA, PMMA and roughed PEEK are demonstrated including both a one-stage and a two-stage process, and at times a vacuum treatment, allowing modification of inner and outer surfaces.

17 Claims, 14 Drawing Sheets

(51) Int. Cl.
*A61L 27/18* (2006.01)
*A61L 27/50* (2006.01)
*C08F 120/18* (2006.01)
*C08G 63/91* (2006.01)
*C08G 65/48* (2006.01)

(52) U.S. Cl.
CPC .......... *C08F 120/18* (2013.01); *C08G 63/912* (2013.01); *C08G 65/48* (2013.01); *A61L 2400/18* (2013.01); *C08J 2333/12* (2013.01); *C08J 2367/04* (2013.01); *C08J 2371/00* (2013.01); *C08J 2371/10* (2013.01)

(58) Field of Classification Search
USPC .................................. 427/2.24, 2.25
See application file for complete search history.

(56) References Cited

U.S. PATENT DOCUMENTS 8,206,774 B2 * 6/2012 Kaplan ............... C08H 1/00
427/2.24
2012/0203326 A1 * 8/2012 Montenegro ......... A61L 31/042
623/1.15

OTHER PUBLICATIONS

Mevellec et al. Grafting Polymers on Surfaces: A New Powerful and Versatile Diazonium Salt-Based One-Step Process in Aqueous Media. Chem Materials, 19, pp. 6323-6330. (Year: 2007).*
Mahjoubi, H. et al. "Surface modification of poly(D,L-lactic acid) scaffolds for orthopedic applications: a biocompatible, nondestructive route via diazonium chemistry" ACS Appl. Mater. interfaces 2014, 6, 9975-9987.

* cited by examiner

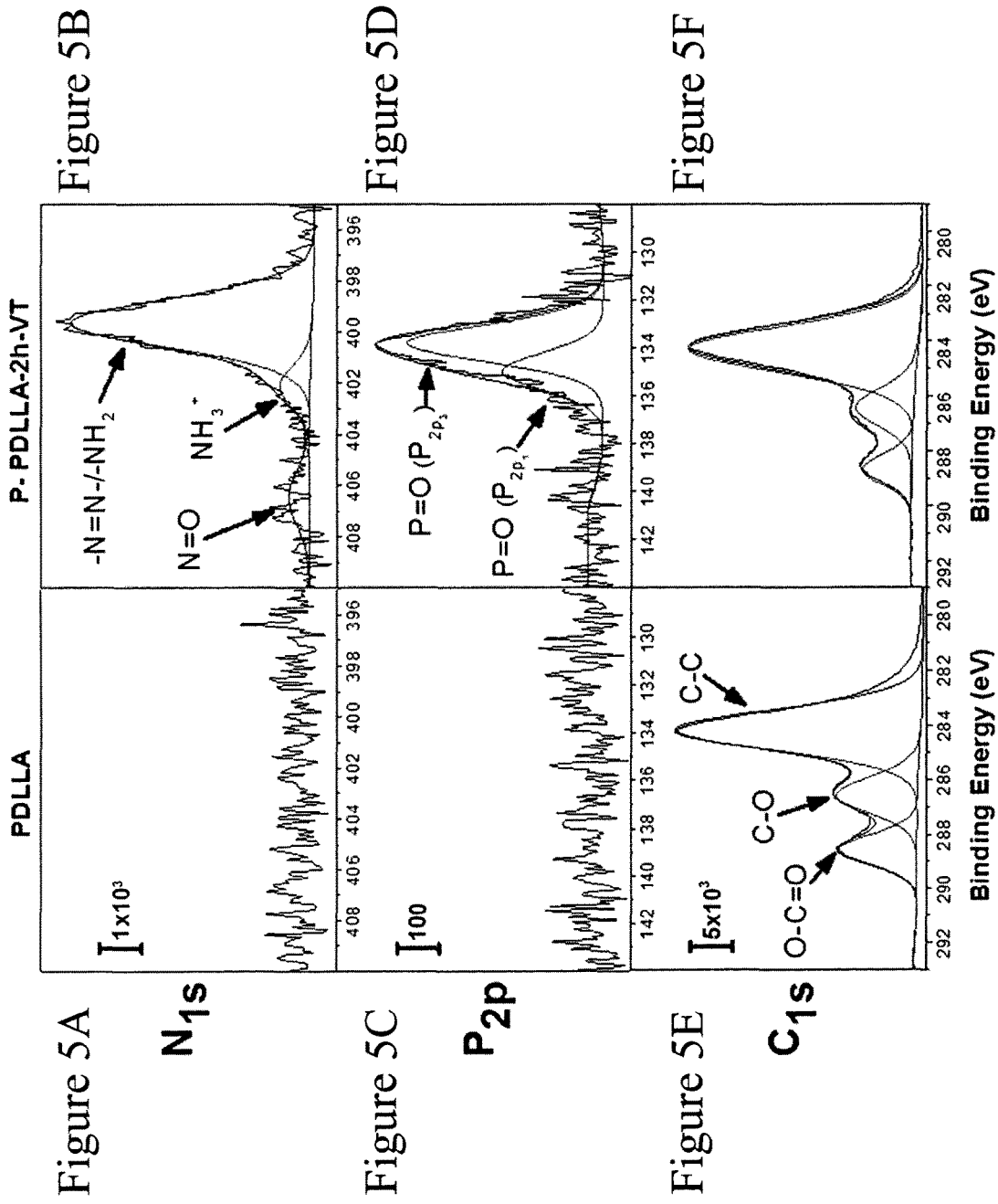

2 μm

2 μm

5 μm

5 μm

5 μm

5 μm

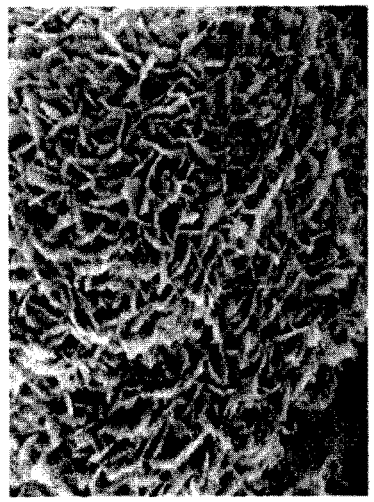
Figure 9
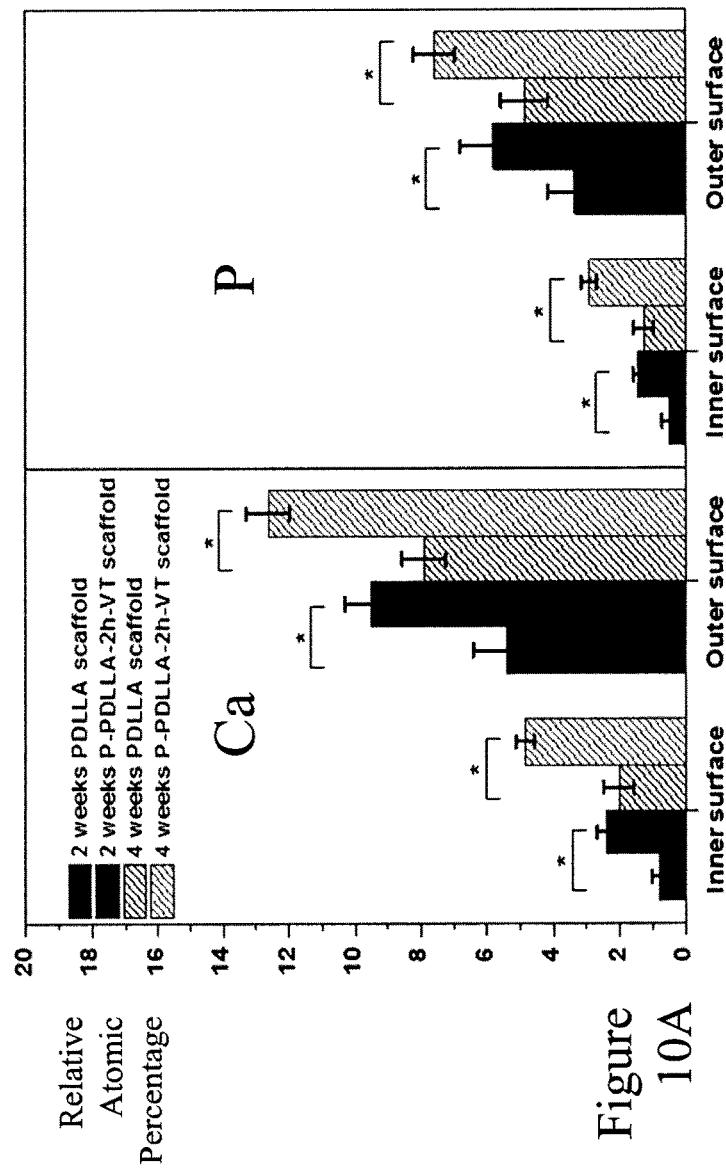
Figure 10A
Figure 10B

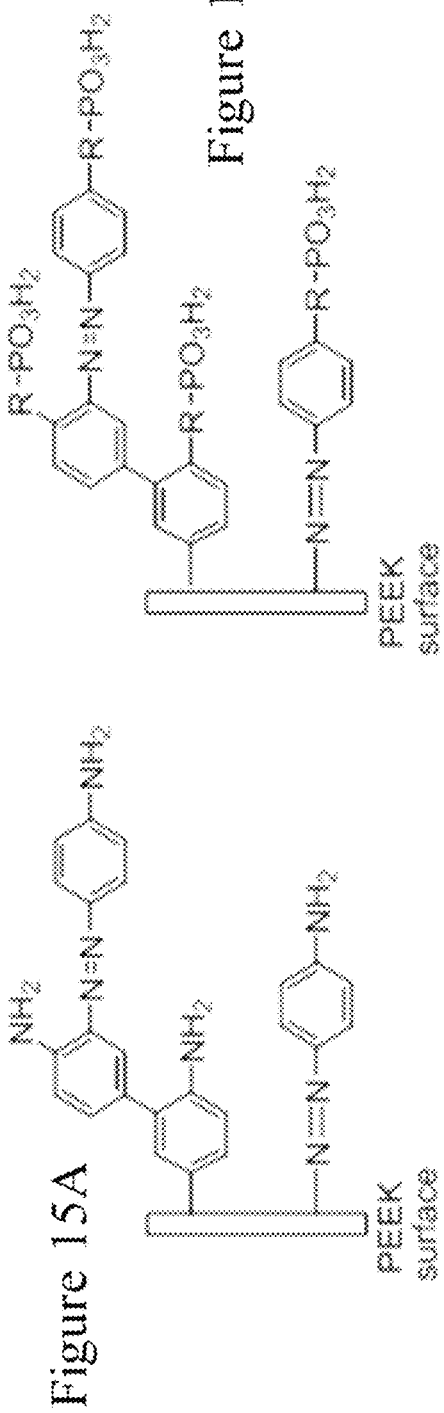
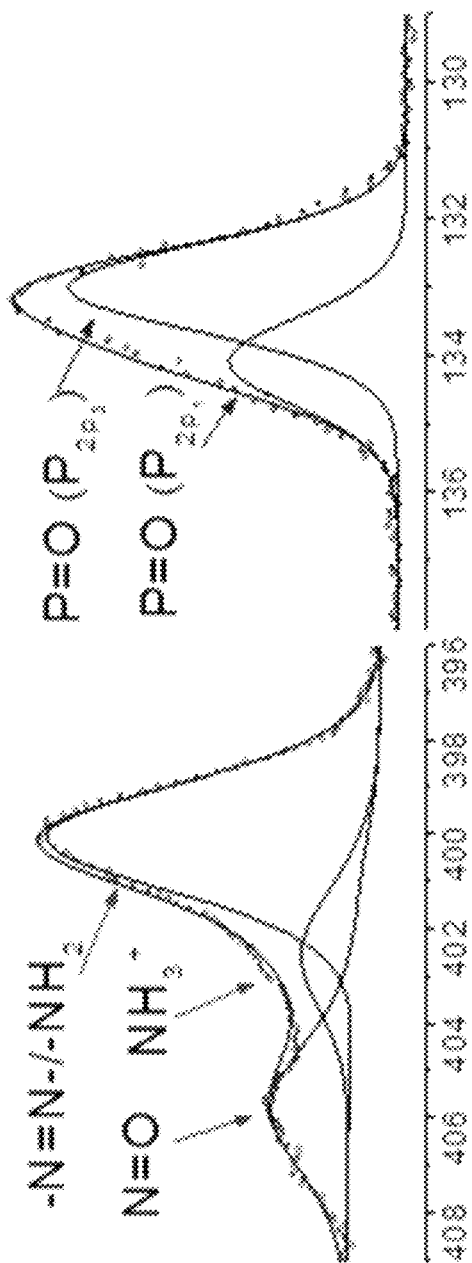
Figure 15A
Figure 15B
Figure 15C
Figure 15D

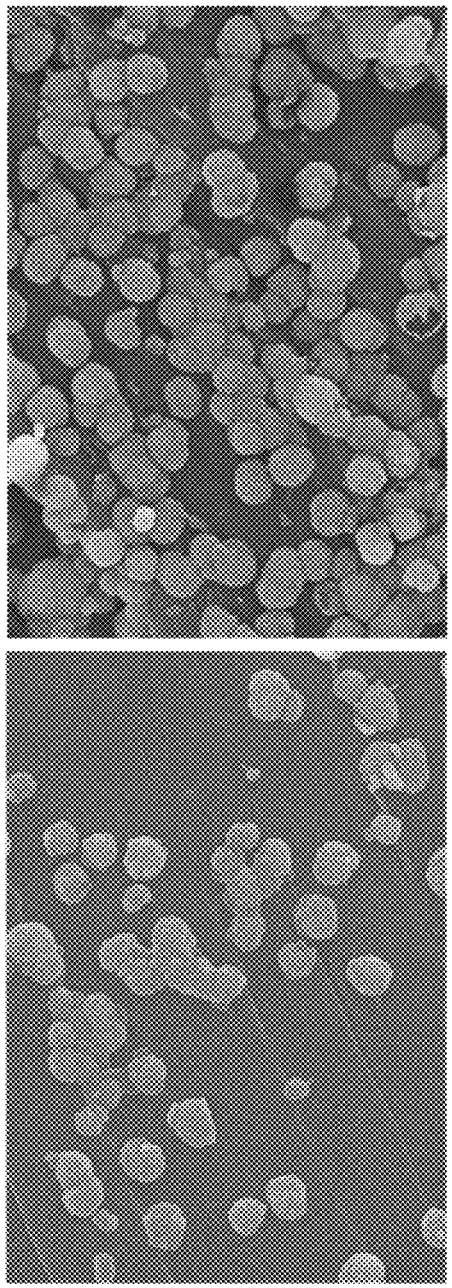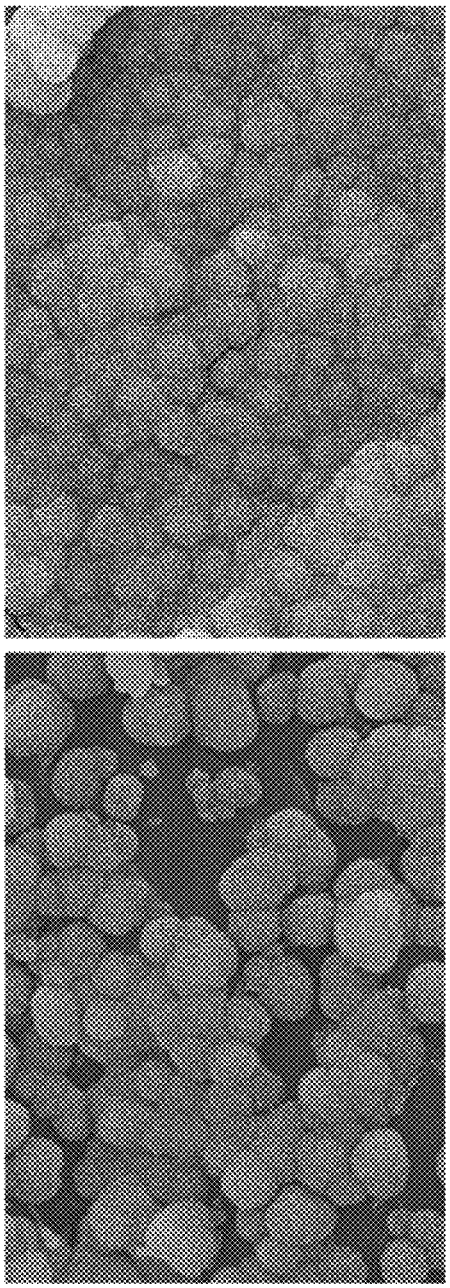

SURFACE MODIFICATION METHODS FOR BIOMEDICAL SCAFFOLDS

CROSS-REFERENCE TO RELATED APPLICATIONS

This application is a U.S. National Phase of International Application No. PCT/CA2015/000378, filed on Jun. 11, 2015 and claiming priority from U.S. provisional patent application 62/010,630 filed on Jun. 11, 2014, and this application claims priority to and the benefit of the above-identified applications, each of which are incorporated by reference herewith in their entirety.)

FIELD OF THE INVENTION

This invention relates to biomedical materials and more particularly to methods of surface modification for enhancing cell adhesion and biocompatibility.

BACKGROUND OF THE INVENTION

Scaffold materials, porous or dense, are used in cell culture and tissue engineering as platforms to enhance cell attachment, proliferation and activity, leading to shorter healing time of injured or missing tissue. These scaffolding materials include, but are not limited to, some metals, certain metallic alloys, different glasses, various ceramics and polymers. In fact many natural and synthetic polymers can be used to fabricate scaffolds for implants. Amongst the most common synthetic polymers are polyesters, such as poly(D,L-lactic acid) (PDLLA), poly(lactic-co-glycolic acid) (PLGA), and thermoplastics, such as polyether ether ketone (PEEK). Polyesters degrade by forming lactic acid and glycolic acid, which are non-toxic, and they are approved by the USA Food and Drug Administration for human clinical use. Accordingly, scaffolds, implants, etc. made with polyesters are commonly used in bone tissue engineering due to their biodegradability, biocompatibility and adequate mechanical properties. In contrast scaffolding employing metals, alloys, ceramics and glasses are typically not biodegradable.

Irrespective of material, the scaffolding surface is the first region that cells contact once the scaffolding material has been implanted and generally determines their reaction to the implant. Despite being biocompatible, most synthetic polymers including polyesters and PEEK are hydrophobic, which is a parameter known to promote non-specific protein adsorption and to prevent maximum adhesion and spreading of cells. Moreover, neither polyesters nor PEEK have any surface group that can specifically enhance cell adhesion, growth or function. As a result surface modification of these materials is crucial to enhance the implant's integration in the body. When the implants are used in orthopedic applications, surface modification can help the formation of hydroxyapatite $(Ca_{10}(PO_4)_6(OH)_2)$ (commonly abbreviated to HA), which is the mineral component of bones through a process known as biomineralization.

In a similar manner, PEEK is a material used within bone implants for its excellent mechanical properties, biocompatibility and radiolucency. However, in common with the user of polyesters for scaffolds, a key limitation is low cell adhesion and bone integration due to the hydrophobic properties of its surface. Accordingly, it would be beneficial to similarly modify the surface of the PEEK implants. Different modification techniques such as such as plasma spray coating, photochemical deposition, radio-frequency magnetron sputtering coating and electron beam deposition have been used in the prior art to add particles, coatings and functional groups to the surface of PEEK. However, major drawbacks include insufficient cohesion, delamination, and high costs of production.

Further, in many instances these processes require line of sight access to the surface being modified which limits their use on complex geometries, porous structures, etc. Accordingly, as with polyesters the surface modification of PEEK would benefit from the availability of a processing methodology to overcome the limitations within the prior art.

Plasma treatment has been successfully applied to modify two-dimensional polymeric surfaces (e.g. films) but in three-dimensional (3D) implants, especially if porous, the technique is less effective as the plasma reacts quickly with the outer surfaces, whilst the inner pores do not get modified. In contrast physical adsorption or chemical hydrolysis (for polyesters) allow implants to be modified both on the outside and inside surfaces. With physical adsorption implants are immersed in a solution containing biomolecules such as natural adhesive proteins and whilst the technique has the advantage of simplicity, it leads to the formation of weak bonds and the biomolecules can detach under physiological conditions. Polyester hydrolysis generates carboxylates and hydroxyl groups which can then bind biomolecules. However, the polymeric backbone of the implant is degraded during this treatment.

Diazonium chemistry is a wet chemistry technique able to modify a variety of surfaces, including polymers, and a "grafting" process can be performed by applying an external potential or exploiting redox reactions occurring between a diazonium salt or its aniline precursor, which is transformed into a reactive radical, and the material to be modified. Accordingly, it would be beneficial to apply this method which has been successful at introducing a number of functional groups, including alkyls, halides, carboxyls, nitro groups, perfluorinated chains, redox species, and dendrimers in other environments to the surface modification of biomedical scaffolds. It would be further beneficial to exploit diazonium chemistry such that the aniline layer formed can be easily reactivated, forming a so-called "self-adhesive surface", and made react with any nucleophilic compound, thus allowing introduction of a wide range of functional groups to the desired surface.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations in the prior art relating to biomedical materials and more particularly to methods of surface modification for enhancing cell adhesion and biocompatibility.

In accordance with an embodiment of the invention there is provided a method of treating a scaffold comprising exposing the scaffold to a diazonium chemistry process to modify the inner and outer surfaces of the scaffold.

In accordance with an embodiment of the invention there is provided a biomedical device comprising a polymeric scaffold, and a surface treatment applied to inner and outer surfaces of the polymeric scaffold, wherein the biomedical device may be employed without at least one of biomineralization and seeding with hydroxyapatite.

In accordance with an embodiment of the invention there is provided a method of treating a material by exposing the material to a diazonium chemistry process to modify the inner and outer surfaces of the material by the addition of a predetermined chemical grouping, wherein the material is one of a metal, an alloy, and a glass.

In accordance with an embodiment of the invention there is provided a method of modifying the surface of a material by the addition of a predetermined chemical grouping, wherein the predetermined chemical grouping is one of a chemical group, a redox species, a dendrimers, a peptide, and a protein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 5A to 5F depict XPS high resolution spectra measured for N1s, P2p and C1s for unmodified PDLLA and P-PDLLA scaffolds via a process according to an embodiment of the invention;

FIG. 9 depicts a high magnification SEM image of the agglomerates present on the surface of a treated P-PDLLA scaffold according to an embodiment of the invention after immersion in SBF;

FIGS. 10A and 10B depict the relative atomic percentages Ca and P on the inner and outer surfaces of untreated and treated P-PDLLA samples according to an embodiment of the invention immersed in SBF;

FIGS. 15A to 15D depict schematically grafted polyaminophenylene (PAP) on a PEEK surface and phosphonate terminated multilayer after attachment of 2-aminoethylphosphonic acid (AEPA) to PAP layer together with N1s and P2p XPS high resolution spectra of PEEK-PT surface according to an embodiment of the invention;

FIGS. 16A to 16D depict high resolution SEM images of PEEK-P, PEEK-PT, PEEK-S and PEEK-ST according to embodiments of the invention after 10 day immersion in SBF solution;

DETAILED DESCRIPTION

Figure 2A:
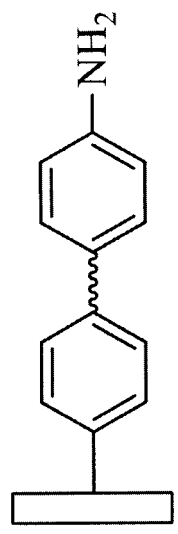
FIGS. 2A depict the general chemical structure of polyaminophenylene (PAP) layers used to described layers similar to those shown within FIGS. 3A to 3D.

The present invention is directed to biomedical materials and more particularly to methods of surface modification for enhancing cell adhesion and biocompatibility.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment or embodiments. It being understood that various changes may be made in the function and arrangement of elements without departing from the spirit and scope as set forth in the appended claims.

A "scaffold" or "scaffolds" as used herein and throughout this disclosure, refers to a structure that is used to hold up, interface with, or support another material. This includes, but is not limited to, such two-dimensional (2D) structures such as substrates and films, three-dimensional (3D) structures such as geometrical objects, non-geometrical objects, combinations of geometrical and non-geometrical objects, naturally occurring structural configurations, and manmade structural configurations. A scaffold may be solid, hollow, and porous or a combination thereof. A scaffold may contain recesses, pores, openings, holes, vias, and channels or a combination thereof. A scaffold may be smooth, textured, have predetermined surface profiles and/or features. A scaffold may be intended to support one or more other materials, one or more films, a multilayer film, one type of particle, multiple types of particles etc. A scaffold may include, but not be limited to, a biomedical implant, an artificial joint, a biomedical container, and a culturing container.

A "polyester" as used herein and throughout this disclosure, refers to a category of polymers that contain the ester functional group in their main chain. This includes, but is not limited to polyesters which are naturally occurring chemicals as well as synthetics through step-growth polymerization, for example. Polyesters may be biodegradable or not. Polyesters may be a thermoplastic or thermoset or resins cured by hardeners. Polyesters may be aliphatic, semi-aromatic or aromatic. Polyesters may include, but not be limited to, those exploiting polyglycolide, polylactic acid (PLA), polycaprolactone (PCL), polyhydroxyalkanoate (PHA), polyhydroxybutyrate (PHB), polyethylene adipate (PEA), polybutylene succinate (PBS), polyethylene terephthalate (PET), polybutylene terephthalate (PBT), polytrimethylene terephthalate (PTT), and polyethylene naphthalate (PEN).

A "thermoplastic" or "thermosoftening plastic" as used herein and throughout this disclosure, refers to a category of polymers that become pliable or moldable above a specific temperature and solidify upon cooling. Thermoplastics may include, but not be limited, polycarbonate (PC), polyether sulfone (PES), polyether ether ketone (PEEK), polyethylene (PE), polypropylene (PP), poly vinyl chloride (PVC), polytetrafluoroethylene (PTFE), polyimide (PI), polyphenylsulfone (PPSU), polychlorotrifluoroethene (PCTFE or PTFCE), florinated ethylene propylene (FEP), and perfluoroalkoxy alkane (PFA).

The ensuing description provides exemplary embodiment(s) only, and is not intended to limit the scope, applicability or configuration of the disclosure. Accordingly, whilst the description and applications with respect to the exemplary embodiments using PDLLA and PEEK are primarily orientated to towards implantable structures/scaffolds it would be evident that the embodiments of the invention may be applied to other applications including, but not limited to, equipment relating to cell culturing, assays, immunoassays, microassays, grafts, replacement skeletal elements, additional skeletal elements, and embedded sensor housings. Rather, the ensuing description of the exemplary embodiment(s) will provide those skilled in the art with an enabling description for implementing an exemplary embodiment or embodiments. It being understood that various changes may be made in the function and arrangement of elements without departing from the spirit and scope as set forth in the appended claims.

The ensuing description provides exemplary embodiment(s) only, and is not intended to limit the scope, applicability or configuration of the disclosure. Accordingly, whilst the description and applications with respect to the exemplary embodiments using polyesters, such as PDLLA, and thermoplastics, such as PEEK, it would be evident that the embodiments of the invention may be applied to other materials including, other polymers; ceramics such as aluminium nitride, aluminium oxide (alumina), zirconium oxide (zirconia), and silicon carbide for example; metals and/or alloys such as titanium, stainless steel, cobalt-chromium, tungsten, tantalum, and nickel-titanium (nitinol) for example; and glass such as silicate glasses, borosilicate glasses, and borate glasses.

Rather, the ensuing description of the exemplary embodiment(s) will provide those skilled in the art with an enabling description for implementing an exemplary embodiment or embodiments. It being understood that various changes may be made in the function and arrangement of elements without departing from the spirit and scope as set forth in the appended claims.

A: Poly(D,L-Lactic Acid) (PDLLA) Scaffolds

A1: Materials and Methods

Poly(D,L-lactic acid) (PDLLA) with an average molecular weight, $M_n$=110,000 g/mo was employed within the embodiments of the invention discussed and presented in respect of FIGS. 1 to 14B. However, it would be evident that the methodologies and processes according to embodiments of the invention may be applied to PDLLA with other average molecular weight. Other materials employed included sodium chloride (NaCl); p-phenylenediamine ($C_6H_4(NH_2)_2$); sodium nitrite ($NaNO_2$); hypophosphorous acid solution (50% wt. in $H_2O$) ($H_3PO_2$); 2-aminoethylphosphonic acid ($H_2NCH_2CH_2P(O)(OH)_2$) (AEPA); sodium hydrogen carbonate ($NaHCO_3$); potassium chloride (KCl); di-potassium hydrogen phosphate trihydrate ($K_2HPO_4.3H_2O$); magnesium chloride hexahydrate ($MgCl_2.6H_2O$); calcium chloride ($CaCl_2$); sodium sulfate ($Na_2SO_4$); tris-hydroxymethyl aminomethane ($NH_2C(CH_2OH)_3$); hydrochloric acid (HCl); tris(hydroxymethyl) aminomethane (commonly referred to as Tris) ($C_4H_{11}NO_3$); and control hydroxyapatite powder (HA).

A2: Scaffold and Thin Film Preparation

Scaffolds were prepared using the solvent casting and particulate leaching method. A 40% (w/w) PDLLA solution in acetone was prepared and mixed with sieved NaCl with particle size ranging from 150 µm≤Particle≤350 µm. The mixture was then casted in a Pyrex Petri dish wherein the formed discs were left to dry in vacuum at room temperature (RT) for 48 hours. Cylindrical samples of 15 mm height and 9 mm diameter were extracted from the discs by hand. The samples were then immersed in deionized (DI) water for 48 hours, with the water changed every 12 hours to leach out the salt particles. The resulting porous scaffolds were then dried in vacuum at RT for 24 hours.

In order to perform the cell culture experiments, PDLLA films (PDLLA-f) as defined in Table 1 were prepared by pouring PDLLA polymer solution inside 35 mm diameter glass Petri dishes wherein the films were dried in vacuum at RT for 24 hours, and a final thickness of ~100 µm was achieved.

A3: Surface Modification

A11: Scaffold Modification

Figures 3A, 3B, 3C, 3D:
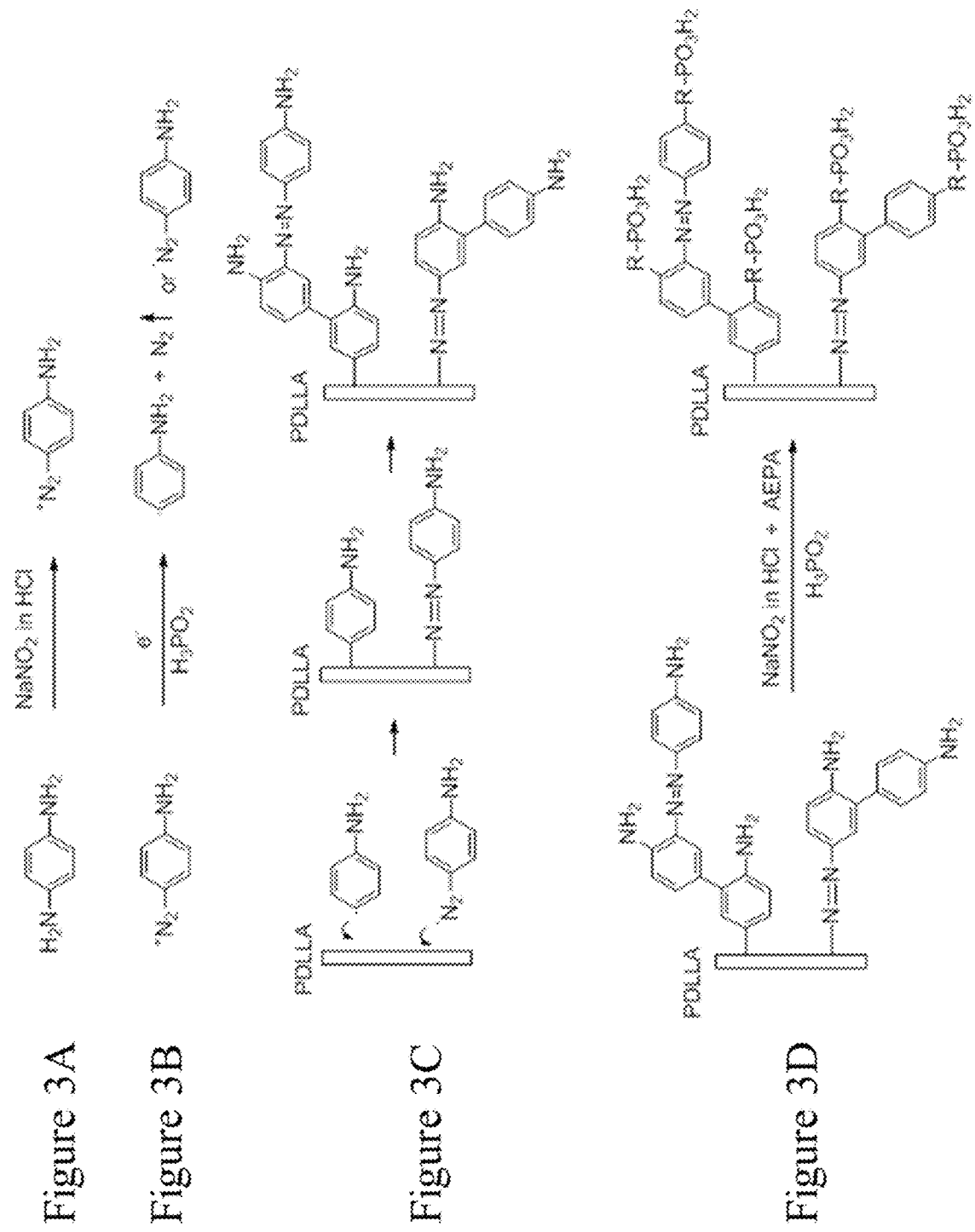
FIG. 3A schematically depicts aminophenyldiazonium cation generation from p-phenylenediamine in solution with a process according to an embodiment of the invention.
FIG. 3B schematically depicts the reduction of the aminophenyldiazonium cations with $H_3PO_2$ a process according to an embodiment of the invention.
FIG. 3C schematically depicts the grafting of aminophenyl and azoaminophenyl radicals onto scaffold surface and formation of the PAP layer with a process according to an embodiment of the invention.
FIG. 3D schematically depicts the grafting of AEPA on the PAP layer formed on the scaffold surface with a process according to an embodiment of the invention.

The PDLLA scaffolds were modified with diazonium chemistry. In order to implement this a solution of 0.1 M aminophenyl diazonium cations ($NH_2$—$C_6H_4$—$N_2^+$) was prepared by dissolving 345 mg of $NaNO_2$ and 540 mg p-phenylenediamine ($C_6H_4(NH_2)_2$) in 50 ml of 0.5M HCl containing 17.85 mM $H_3PO_2$. This is depicted in FIGS. 3A to 3C respectively. Two batches of ten PDLLA scaffolds were stirred in this solution for either 1 or 2 hours to bind the diazonium cations to PDLLA, thus yielding amino-functionalized scaffolds. The samples were then rinsed and sonicated in DI water for 10 minutes to remove physisorbed diazonium cations. The amino-functionalized scaffolds were then immersed and stirred for either 1 or 2 hours in a 10 mM solution of AEPA ($H_2NCH_2CH_2P(O)(OH)_2$), see FIG. 1A, prepared in a 0.5 M solution of HCl containing also 5 mM $NaNO_2$ and 17.85 mM $H_3PO_2$. The samples were then rinsed and sonicated in DI water for 10 minutes and dried for 48 h in vacuum at RT. These samples being referred to as "P-PDLLA-1h" and "P-PDLLA-2h" (see Table 1 for sample name abbreviations), where the letter "P" before PDLLA refers to the introduction of phosphonate groups on the scaffold surface.

In order to achieve a homogenous modification on the outer and inner scaffold surfaces, a batch of eight scaffolds were treated in different manners, using a vacuum treatment. The reaction solution described above was frozen by liquid nitrogen in a vented Erlenmeyer flask, and the scaffolds and a magnetic stirrer were placed on top of the frozen solution. The flask was then connected to vacuum to eliminate the air inside the scaffold pores, and then brought to RT. As the solution thawed, the scaffolds and the stir bar dropped in it, and the functionalization proceeded as explained above for the "P-PDLLA-2h" samples. These samples were named "P-PDLLA-2h-VT", where "VT" stands for "vacuum treatment" (see Table 1).

TABLE 1

Summary of Sample Name Abbreviations and Corresponding Preparation

| Sample Name | Form | Duration of First Step (Amination) | Duration of Second Step (Phosphonation) | Vacuum Treatment |
|---|---|---|---|---|
| PDLLA | Scaffold | None | None | N/A |
| P-PDLLA-1h | Scaffold | 1 hour | 1 hour | NO |
| P-PDLLA-2h | Scaffold | 2 hours | 2 hours | NO |
| P-PDLLA-2h-VT | Scaffold | 2 hours | 2 hours | YES |
| PDLLA-f | Film | None | None | N/A |
| N-PDLLA-f | Film | 2 hours | None | N/A |
| P-PDLLA-f | Film | 2 hours | 2 hours | N/A |

A3.2: Film Modification

Some of the PDLLA films prepared in 35 mm glass Petri dishes were left as such, and were used as control samples (PDLLA-f, see Table 1). Other films were further modified with diazonium chemistry, by immersing them for 2 hours in 50 ml of 0.5 M HCl solution containing 345 mg $NaNO_2$, 540 mg p-phenylenediamine ($C_6H_4(NH_2)_2$) and 17.85 mM $H_3PO_2$. This led to a batch of amino-functionalized films (see FIGS. 3A to 3C, "N-PDLLA-f" samples, see Table 1). A second batch of samples was further treated following the same route used to introduce phosphonate groups on the scaffolds: the films were immersed for 2 hours in a 10 mM solution of AEPA ($H_2NCH_2CH_2P(O)(OH)_2$), prepared in a 0.5 M solution of HCl containing also 5 mM $NaNO_2$ and 17.85 mM $H_3PO_2$ (see FIG. 3D). These samples are referred to as "P-PDLLA-f" (see Table 1).

A4: Immersion Tests

A batch of eight unmodified PDLLA scaffolds and one consisting of eight "2 h vacuum treated" samples were used for the immersion tests in simulated body fluid (SBF). The SBF solution was prepared with the composition presented in Table 2. The scaffolds were immersed and stirred in SBF inside an incubator at 37° C. for two or four weeks. The SBF solution was changed every 3 days to better mimic the constant concentration present in body fluids.

TABLE 2

SBF Reagents and their Concentration

| Reagent | Concentration (ppm) |
|---|---|
| NaCl | 8035 |
| $NaHCO_3$ | 355 |
| KCl | 225 |
| $K_2HPO_4 \cdot 3H_2O$ | 231 |
| $MgCl_2 \cdot 6H_2O$ | 311 |
| $CaCl_2$ | 292 |
| $CaCl_2$ | 72 |
| $C_4H_{11}NO_3$ (Tris) | 6118 |

A5: Characterization

The surface composition of the scaffolds was characterized by X-ray photoelectron spectroscopy (XPS) using a K-alpha spectrometer, equipped with an Al-Kα X-ray source (1486.6 eV, 0.843 nm) and using an X-ray spot diameter of 400 μm. To prevent charging on the polymeric scaffolds, the samples were hit with a flood gun shooting low energy electrons during the measurement. Scaffolds were cut using a razor blade and measurements were taken along the cross section of the samples.

Gel permeation chromatography (GPC) was conducted on a PDLLA sample and on both bare and surface modified PDLLA scaffolds, using a chromatographer. The GPC was equipped with three high resolution columns which were able to measure molecular weights in the range of 100 $gmol^{-1} \leq MW \leq 10^5$ $gmol^{-1}$. All columns were operated at 40° C. and with a mobile phase flow rate of 0.3 mL $min^{-1}$ during analysis. The GPC was equipped with both ultraviolet and differential refractive index detectors with measurements calibrated using poly(methyl methacrylate) (PMMA) standards dissolved in tetrahydrofuran (($CH_2)_4O$; THF) at 40° C.

The surface morphology of the scaffolds after immersion in SBF was characterized using a Field Emission scanning electron microscope (FE-SEM) wherein the samples were analyzed without any coating and images were collected at an acceleration voltage of 0.5 kV.

Raman spectra of the scaffolds after immersion in SBF were recorded on a setup composed of a confocal Raman microscope connected to a stand-alone FT-Raman spectrometer. The 1032 nm source laser being coupled via a fiber optic cable through the microscope, and the spectra were acquired using a 40× objective, ranging from 0 to 3600 $cm^{-1}$ with 256 scans at 3.5 $cm^{-1}$ resolution. The collected signal was coupled to the detector via a second fiber optic cable.

Infrared (IR) spectroscopy was performed with the particles precipitated on the scaffolds after immersion in SBF extracted by dissolving the polymeric scaffold matrix in acetone, stirring for 2 hours. The powders were separated from the polymeric solution by filtering and vacuum drying for 24 hours. IR spectra of the extracted particles were collected on a FT-IR spectrometer in diffuse reflectance (DRIFT) mode. The powders were diluted with an approximate 50% weight/weight ratio of KBr, and the spectra were collected from 400 to 4000 cm$^{-1}$ using a triglycine sulfate (TGS) DTGS detector, with 256 scans at 4 cm$^{-1}$ resolution.

A6: Cell Culture

Chondrogenic ATDC5 cells and Murine MC3T3-E1 preosteoblasts (subclone 14) were cultured in Minimum Essential Medium alpha containing 2 mM L-Glutamine (MEM α) supplemented with 10% Fetal Bovine Serum and 100 U/ml penicillin-streptomycin at 37° C. under 5% $CO_2$ in a humidified incubator. Prepared PDLLA, aminated and phosphonated films in 35 mm glass Petri dishes were sterilized by immersion in absolute ethanol for 10 minutes before seeding the cells. ATDC5 and MC3T3-E1 cells were seeded in triplicates on the films at densities of $2.0 \times 10^6$ cells·cm$^{-2}$ and $55.0 \times 10^6$ cells·cm$^{-2}$ for the proliferation and mineralization assays, respectively. To induce mineralization, cells were differentiated by adding ascorbic acid (100 μg·ml$^{-1}$), β-glycerol phosphate (5 mM) and dexamethasone (10 mM) to the culture medium.

A7: Alamanr Blue and MTT Reduction Assays for Assessment of Cell Viability/Metabolic Activity In order to examine cell viability/metabolic activity in each culture, Alamar Blue solution was directly added to the medium after 4 days of culture at a 100 μM final concentration. The reduction of Alamar Blue was measured fluorometrically (excitation at 560 nm and emission at 610 nm) using a microplate reader after 1, 2, 3 and 4 hours of incubation at 37° C.

A8: Evaluation of Cell Culture Mineralization by Alizarin Red Staining

For quantification of deposited minerals, ATDC5 and MC3T3-E1 cultures grown in the differentiation medium for 3 weeks were stained with 40 mM Alizarin Red solution (pH 4.0) for 5 minutes and thoroughly washed in deionised water. Images were taken at room temperature using a light microscope with 10× objective. Images were captured using a digital camera and processed using Adobe™ PhotoShop. For quantification of the deposited minerals, bound dye was dissolved in 10% glacial acetic acid and measured spectrophotometrically at 405 nm using a microplate reader.

A9: Statistical Analysis

All results are shown as standard deviation of the mean. Statistical analyses were performed by Student's t-test or one way analysis of variables (ANOVA) with p<0.5 considered significant as indicated by a single asterisk.

A10: Results and Discussion

Surface modification of scaffolds for tissue engineering is crucial to improve their effectiveness and success once implanted. The inventors exploit diazonium chemistry to modify 3D PDLLA scaffolds homogenously and non-destructively. Via this technique, an aryldiazonium salt is dissolved in a weak acidic solution to generate aryldiazonium cations, see FIG. 1B. These cations can be easily reduced to form stable radicals that are able to attack and bind to many different surfaces.

Referring to FIG. 3 the process flow employed by the inventors to modify the PDLLA scaffolds is presented. In this method, the aryldiazonium cations are formed in-situ through the reduction of p-phenylenediamine. In the first step depicted in FIG. 3A, one equivalent of $NaNO_2$ was added to an acidic solution of p-phenylenediamine. This step leads to the predominant formation of the aminophenyl monosubstituted diazonium cations $NH_2$—$C_6H_4$—$N^{2+}$ as shown in FIG. 3A. This arises as bisdiazonium cations are more difficult to form for electrostatic reasons and because the second amine left on the monodiazonium cation is less reactive towards diazotation.

In the second step depicted in FIG. 3B, the aminophenyl diazonium cation was reduced to a stable aminophenyl radical ($NH_2$—$C_6H_4$*), using $H_3PO_2$ as a reducing agent. The reduction of aromatic diazonium cations leads to the formation of aminophenyl radicals ($NH_2$—$C_6H_4$*). Aminodiazenyl radicals ($NH_2$—$C_6H_4$*, shown in FIG. 3B) were speculated to be formed as well although this point is not proven.

Within the third step depicted in FIG. 3C, the scaffolds are immersed in the solution containing the radicals formed by the reduction of diazonium cations, and a multilayer structure similar to that shown in FIG. 3C is formed on their surface. Within this specification this later will referred to a "polyaminophenylene" (PAP) layer which, as depicted in FIG. 2A has a structure similar to that shown with the process described according to embodiments of the invention in FIG. 3C, and accordingly the inventors refer to the layers within embodiments o the invention with this structure as PAP layers. The PAP layer contains azo (N=N) bridges, possibly because of the reaction with the aminodiazenyl radicals, or via other more complex routes.

Figure 2B:
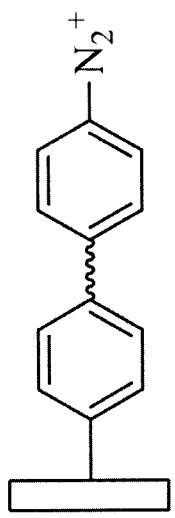
FIGS. 2B depict the general chemical structure of polydiazophenylene (PDP) layers used to described layers similar to those shown within FIGS. 3A to 3D.
Figure 1A:
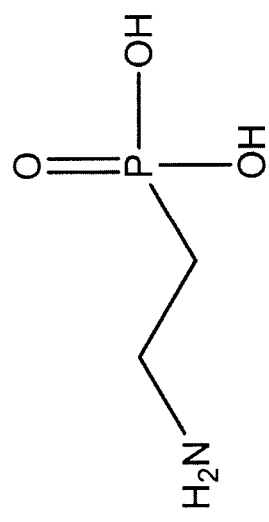
FIG. 1A depicts the chemical structure of 2-aminoethyl-phosphonic acid (AEPA)
Figure 1B:
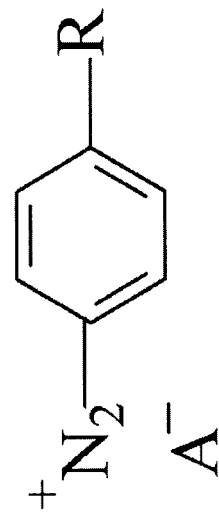
FIG. 1B depicts the general chemical structure of an aryldiazonium cation, where R stands for a variety of functional groups, which can be organic or organometallic substituents, and A– is the counter anion.

Within the fourth step depicted in FIG. 3D, the aminated scaffolds are washed and placed in an acidic solution containing AEPA, $NaNO_2$, and $H_3PO_2$.$NaNO_2$ is added to diazotize the PAP layer, thus transforming it into a "polydiazophenylene" film (PDP), which, as depicted in FIG. 2B has a structure similar to that shown with the process described according to embodiments of the invention in FIG. 3D, and accordingly the inventors refer to the layers within embodiments o the invention with this structure as PDP layers. The diazonium cations on the PDP layer are then reduced to radicals again by $H_3PO_2$. These radicals react with AEPA, resulting in the formation of a phosphonate-terminated multilayer with structure similar to that shown in FIG. 3D. The exact product and the mechanism of this coupling reaction is not entirely evident, however its success and the presence of phosphonate terminal groups are proven by our XPS results (see Table 3 and FIGS. 5A to 5F for example). The coupling is thought to occur because of the reaction between nucleophilic groups and the diazonium cations formed upon reduction of the PAP layer with $NaNO_2$. However, triazenes should be formed by reaction between diazonium cations and primary amines, and these compounds are highly unstable.

Figure 4B:
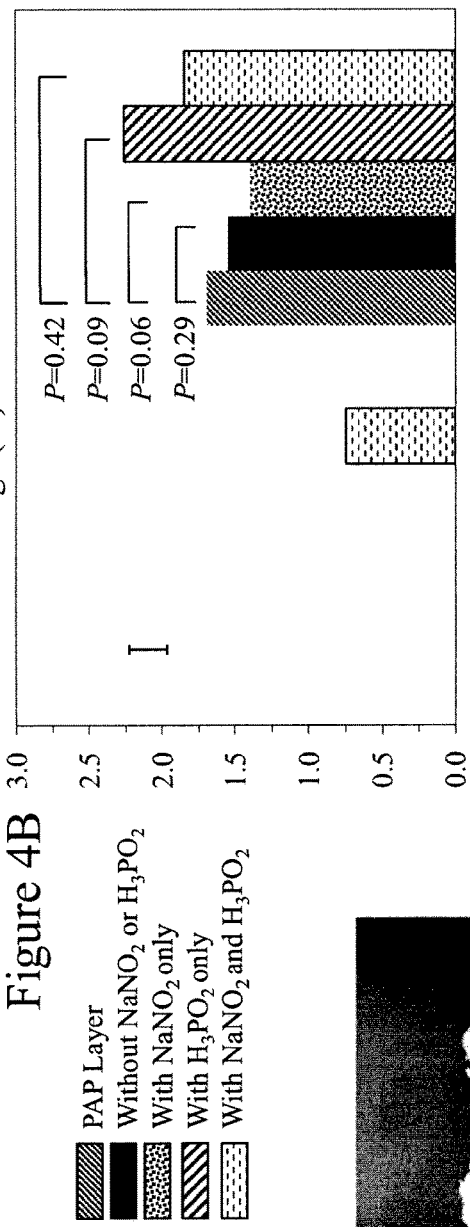
FIG. 4B depicts XPS data for PDLLA samples showing the requirement for both $NaNO_2$ and $H_3PO_2$ to achieve AEPA binding to the PAP layer.
Figure 4A:
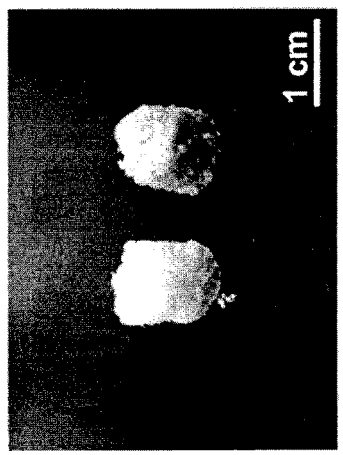
FIG. 4A depicts an untreated and treated PDLLA scaffold as the result of a process according to an embodiment of the invention.
Figure 6:
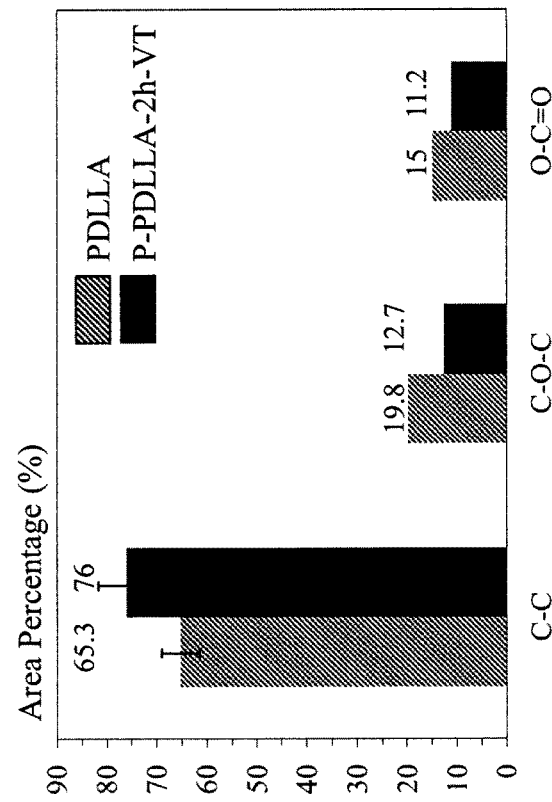
FIG. 6 depicts the relative amounts of different carbon species found on scaffolds before and after treatment with a process according to an embodiment of the invention.

Referring to FIG. 4A there are depicted a control PDLLA scaffold and a P-PDLLA-2 h scaffold (see Table 1 for sample name abbreviations). The true brownish color of the treated scaffold (right scaffold in FIG. 4A) is due to the presence of azo bridges (—N=N—). This visually shows the successful formation of the PAP layer shown in the third and fourth steps depicted in FIGS. 3C and 3D. Accordingly, the inventors believe that the coupling between AEPA and PDP proceeds via a radical mechanism as a result of the addition of $H_3PO_2$.

The inventors accordingly performed additional experiments in the absence of $H_3PO_2$ and shown that AEPA is not bound to the PDP layer in this case. To undertake this the inventors prepared PDLLA films by pouring an 8.0 g/100 ml PDLLA solution into Petri dishes with 100 mm diameter. The films were dried in vacuum at RT for 24 hours, and achieved a final thickness of 500 μm before being sampled by taking 9 mm diameter samples from the larger films. The PAP layer was prepared on the films as described in respect of FIGS. 3A to 3C wherein the films were immersed and stirred the films for 2 hours in 50 ml of 0.5 M HCl containing 345 mg $NaNO_2$, 540 mg p-phenylenediamine and 17.85 mM $H_3PO_2$. Following this, the inventors attempted the binding of AEPA to this layer using four different strategies:
1) Without $NaNO_2$ or $H_3PO_2$: Amino-functionalized films were immersed and stirred for 2 hours in a 10 mM solution of AEPA prepared in 0.5 M HCl;
2) With $NaNO_2$ only: Amino-functionalized films were immersed and stirred for 2 hours in a 10 mM solution of AEPA prepared in 0.5 M HCl containing also 5 mM $NaNO_2$;
3) With $H_3PO_2$ only: Amino-functionalized films were immersed and stirred for 2 hours in a 10 mM solution of AEPA prepared in 0.5 M HCl containing also 17.85 mM $H_3PO_2$; and
4) With $NaNO_2$ and $H_3PO_2$: Amino-functionalized films were immersed and stirred for 2 hours in a 10 mM solution of AEPA prepared in 0.5 M HCl containing also 5 mM $NaNO_2$ and 17.85 mM $H_3PO_2$.

In each case the samples were then rinsed and sonicated in DI water for 10 minutes and dried for 48 h in vacuum at RT after which the surface atomic percentages of P and N within the films were detected by XPS. These results are depicted in FIG. 4B. These results clearly indicate that a noticeable amount of P is detected only when both $NaNO_2$ and $H_3PO_2$ are used. In the absence of $NaNO_2$ (samples 1 and 3), the PAP layer cannot be converted into PDP (i.e. the amino groups are not diazotized). In the absence of $H_3PO_2$ (condition 2), most likely, unstable triazenes were formed, which dissociated and did not allow for a stable coupling of AEPA on the surface. A successful coupling is detected only in the presence of both $NaNO_2$ and $H_3PO_2$ (condition 4).

The variations in the amounts of N detected on the surface of the films is not statistically significant when comparing any of the four conditions of the coupling step to the first step (PAP layer). This is probably due to the fact that the thickness of the PAP layer is somewhat variable from sample to sample, and the addition or removal of N due to the coupling step is not sufficient to make the overall N amount vary significantly. The almost statistical significant decrease in N observed for condition 2 might be related to the instability and reactivity of the triazenes formed.

Referring to Table 3 there are presented the atomic compositions of the inner and outer surfaces measured by XPS on the P-PDLLA-1 h, P-PDLLA-2h and P-PDLLA-2h-VT samples. Almost double amounts of N and P were measured on the outer surfaces of the 2 hour treated samples compared with the 1 hour treated samples. This increase indicates that the amount of functional groups introduced on the surface can be controlled by simply changing the reaction time. The survey data measured along the cross-section of both P-PDLLA-2h and P-PDLLA-1h showed that the functionalization was not homogenous, and the inner core contained a much smaller amount of both N and P compared to the outer surfaces, which were in direct contact with the reaction solution. In order to address this problem, the inventors functionalized the samples under vacuum, to remove the air trapped in the scaffold pores and generate a driving force for the diazonium solution to penetrate throughout the core of the scaffold. This resulted in a much more homogenous functionalization, involving the same amount of grafted AEPA on the outer and inner surfaces of the scaffolds, as can be seen by the almost identical P percentage. A higher amount of N was still visible on the outer surfaces of the scaffolds, possibly due to the fact that in the third step (FIG. 3C) the covalent bonding of the aryldiazonium cations was so fast that a larger number of them reacted with the scaffold surface despite the driving force created by the vacuum inside the scaffold pores. Some samples contained traces of chlorine, possibly because of incomplete removal of HCl during the rinsing.

TABLE 3

XPS survey data measured on surface modified scaffolds (see Table 1 for sample descriptions). All data are averages of at least 10 values, ± the standard deviation.

| Sample | Surfaces | Relative Elemental Composition on the Surface (atom %) | | |
|---|---|---|---|---|
| | | N | P | Cl |
| P-PDLLA-1h | Outer | 1.6 ± 0.3 | 0.7 ± 0.2 | — |
| | Inner | — | — | — |
| P-PDLLA-2h | Outer | 3.4 ± 0.2 | 1.3 ± 0.1 | 0.1 ± 0.0 |
| | Inner | 1.4 ± 0.2 | 0.3 ± 0.2 | — |
| P-PDLLA-2h VT | Outer | 3.9 ± 0.1 | 1.1 ± 0.2 | 0.3 ± 0.1 |
| | Inner | 2.5 ± 0.2 | 1 ± 0.1 | 0.2 ± 0.1 |

The structure of the AEPA layer bound to the scaffolds is better understood by analyzing high resolution XPS spectra. FIGS. 5A to 5F show high resolution spectra for N1s, P2p and C1s before and after treatment via diazonium chemistry. While no N is present on the scaffolds before the treatment (FIG. 5A), the N1s spectrum for the P-PDLLA-2h-VT sample (FIG. 5B) shows the presence of amino groups (peak at binding energy (BE) of 399.4 eV), which was previously reported for films prepared by diazonium chemistry via reduction of aminophenyl groups. This peak actually contains a component also related to azo bridges (—N=N—), normally found at 400 eV. The presence of azo bridges has been previously reported on PDP layers, and its origin has been attributed either to the reaction of aminodiazenyl radicals, or to the reaction between aryl radicals and diazonium cations. The shoulder found at higher BE (401.9 eV) can be related to the presence of ammonium groups (—$NH_3^+$). The formation of ammonium groups explains the presence of chlorine found in the XPS survey spectra of some of the treated scaffolds as shown in Table 3, since chlorine can act as counter ion for the positively charged ammonium groups. The peak positioned at higher BE (406 eV) indicates the presence of nitro groups, but the reason for the formation of these species is unclear. It is possible that they may form upon reaction with impurities, or they may relate to the use of $NaNO_2$ in the coupling.

While no P was present on the untreated samples (FIG. 5C), the P2p spectra measured on the treated samples (FIG. 5D) showed a peak centered at 134.1 eV, which well corresponds to a phosphonate group. Previous researchers have reported P2p peaks with BE ranging from 132.4 eV≤BE≤135.8 eV for titanium and tantalum oxide surfaces modified with phosphonic acid for biomedical applications.

Three components can be clearly distinguished on the C1s spectra of PDLLA scaffolds both before and after treatment (FIGS. 5E and 5F), which can be related to C—C, C—O—C and O=C—O bonds, with BEs of approximately 284.4 eV, 286.6 eV, and 288.6 eV, respectively. While the position of these components does not change significantly before and after treatment, their relative amount does (see FIG. 6). The increase in the relative amount of C—C bonds with respect to C—O—C and C=O bonds observed after treatment confirms the formation of the PAP layer and the coupling of AEPA on the surface of the scaffolds, since neither the PAP layer nor AEPA contain any carboxyl or carbonyl groups.

The XPS results confirmed that AEPA was successfully bound to PDLLA scaffolds via diazonium chemistry. The amount of bound molecules could be controlled by changing the reaction time, and a homogenous modification was achieved using vacuum impregnation.

Figure 7A:
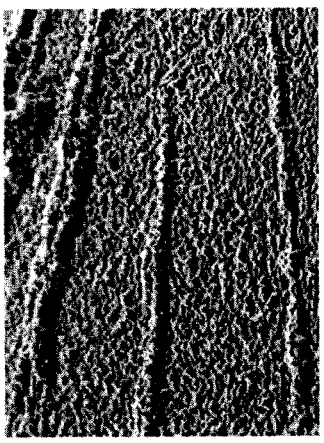
FIGS. 7A and 7B depict SEM images of the surfaces of untreated scaffolds and treated scaffolds.
Figure 7B:

In order to verify that the acidic conditions used during the diazonium treatment did not cause degradation of the PDLLA structure, the inventors analyzed the samples by GPC. As shown in Table 4, and polydispersity index (PDI) measured on a sample of PDLLA, an untreated PDLLA scaffold and a P-PDLLA-2h-VT scaffold are approximately the same. This shows that the acidic conditions of the reaction solution does not cause degradation and changes in the polymer structure. Some changes in surface morphology occurred after the treatment, as shown in FIGS. 7A and 7B. While the untreated scaffolds present a smooth surface (FIG. 7A), the P-PDLLA-2h-VT samples show a rougher surface (FIG. 7B). This can be related to the formation of the PAP layer (FIG. 3C), as previously observed when a similar procedure was used to functionalize smooth surfaces like graphite. However, no signs of surface degradation such as formation of larger pores were observed, contrary to what was previously found when PDLLA scaffolds were treated by hydrolysis.

which still showed areas free from agglomerates. The agglomerates observed on the treated samples were bigger than those formed on the untreated ones. After 4 weeks of immersion (FIGS. 8C and 8D), the agglomerates increased in size for both the unmodified and the treated scaffolds; however, again, larger and more abundant agglomerates were observed on the treated samples. A high magnification image of the particles formed on the treated scaffolds immersed in SBF for 2 weeks is shown in FIG. 9. A similar morphology was observed on all other samples, showing spherulitic particles composed by thin platelets. This morphology is typically observed for HA precipitation from solutions with Ca and P concentration close to plasma.

The inventors then performed XPS to obtain a more quantitative evaluation of the amount of precipitates formed on the scaffolds, as well as to understand their composition. XPS survey spectra showed the presence of Ca and P on the scaffold surfaces after SBF immersion (FIGS. 10A and 10B respectively). The Ca/P ratio measured on the precipitates found both on the inner and on the outer surfaces of the untreated scaffolds after both 2 and 4 weeks immersion was 1.6±0.2, while for the treated scaffolds was 1.7±0.2, which suggests that HA was formed on all samples. Larger amounts of both Ca and P were observed outside than inside the scaffolds (FIG. 7), probably because the HA particles deposited on the outer surface prevented the diffusion of $Ca^{2+}$ and $PO_4^{3-}$ ions inside the scaffolds. This suggests that most of the HA nucleation and growth occurred on the areas of the scaffolds more directly exposed to SBF. Higher amounts of both Ca and P were found on the treated than on the untreated samples, both on the outer and inner surfaces of the scaffolds, both at 2 and at 4 weeks immersion. This confirms the qualitative SEM observations, and suggests that the modification with phosphonate groups caused a larger number of $Ca^{2+}$ cations to be attracted towards the scaffold surfaces, thus increasing the number of HA nucleation sites and the overall amount of HA particles deposited on the scaffolds.

Figure 11:
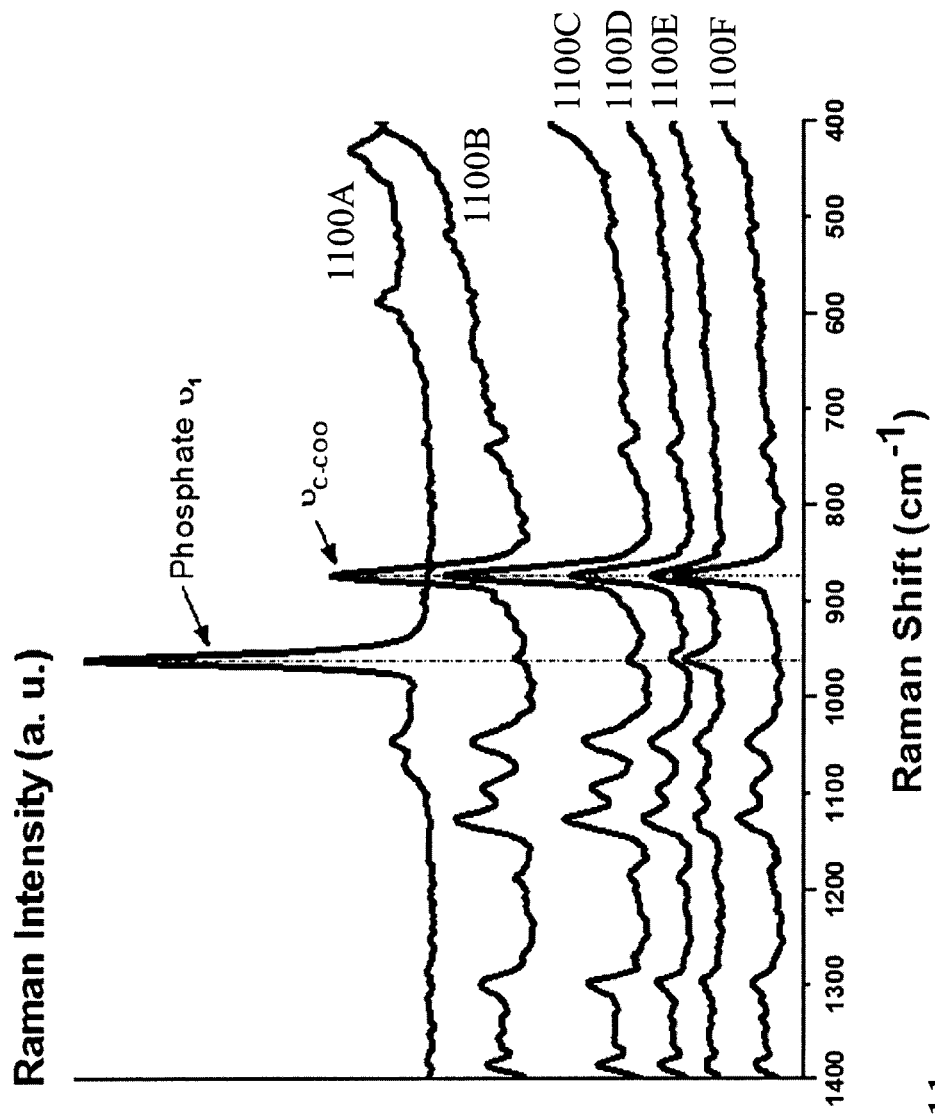
FIG. 11 depicts Raman spectra of untreated scaffolds after immersion in SBF together with treated P-PDLLA according to an embodiment of the invention after immersion in SBF together with PDLLA scaffold and HA control samples.

To confirm that the particles were indeed HA, the inventors performed both Raman and IR spectroscopy on the samples. FIG. 11 shows the spectra collected as follows: Second and fourth traces 1100B and 1100D respectively are untreated scaffolds after 2 and 4 weeks immersion in SBF;

TABLE 4

Mn and PDI obtained by GPC for PDLLA, untreated PDLLA scaffolds, and P-PDLLA-2h-VT scaffolds

|  | PDLLA polymer | PDLLA scaffold | P-PDLLA-2h-VT scaffold |
| --- | --- | --- | --- |
| $\overline{M_n}$ (g/mol) | 202,645 | 195,718 | 200,280 |
| PDI | 1.82 | 1.69 | 1.74 |

Figure 8A:
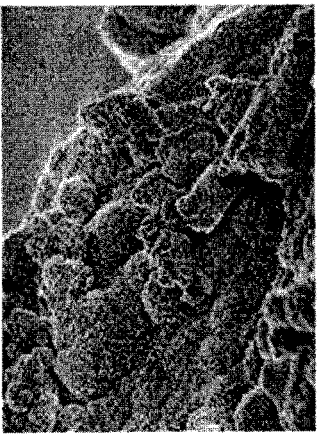
FIG. 8A to 8D depict SEM images of untreated and P-PDLLA treated scaffolds according to an embodiment of the invention after immersion in SBF.
Figure 8B:
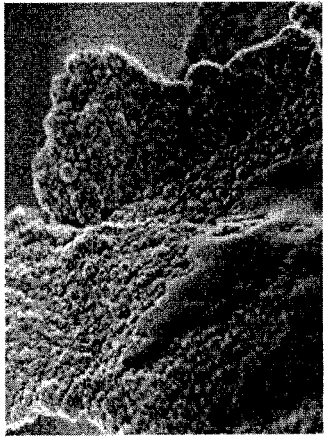
Figure 8C:
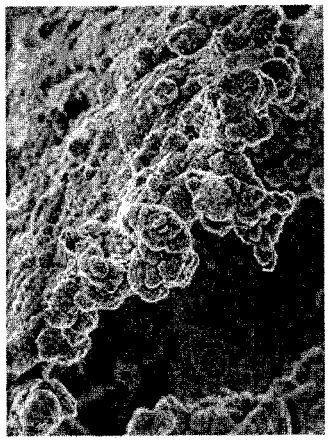
Figure 8D:
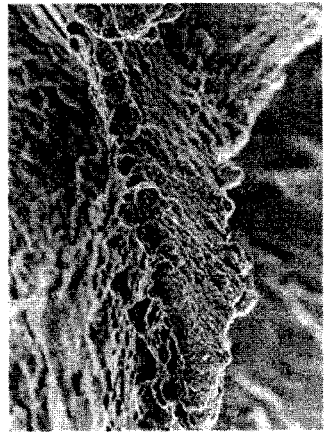

Having proven that the scaffolds could be homogenously modified without degrading their polymeric structure, the inventors immersed them in SBF for up to four weeks. The goal of this experiment was to check if the phosphonate groups introduced were able to enhance HA precipitation on the scaffolds. Referring to FIGS. 8A to 8D respectively, there are depicted SEM images of the unmodified and P-PDLLA-2h-VT scaffolds after 2 and 4 weeks of immersion in SBF. While no particles were observed before SBF immersion on both treated and untreated scaffolds (FIGS. 7A and 7B), after 2 weeks of immersion agglomerated particles are clearly evident on the surface of both types of scaffolds (FIGS. 8A and 8B). The treated samples were covered more homogeneously than the untreated ones, Third and fifth traces 1100C and 1100E respectively are P-PDLLA-2h-VT scaffolds after 2 and 4 weeks immersion in SBF;

Sixth trace 1100F is a control PDLLA scaffold; and

First trace 1100A is HA.

The four phosphate bands, Band 1 (964 $cm^{-1}$), Band 2 (430 $cm^{-1}$), Band 3 (1046 $cm^{-1}$) and Band 4 (589 $cm^{-1}$) are clearly visible on the HA spectrum. Most of the peaks observed on the spectra relative to the scaffolds immersed in SBF relate to the PDLLA matrix, as can be seen by comparing them with the PDLLA spectrum. This is due to the fact that Raman is less surface sensitive than XPS (an approximately 1 μm thick surface layer is analyzed by Raman, and 3-10 nm by XPS), and thus more of the sample substrate is picked up by Raman than by XPS. Despite this, the Band 1 phosphate peak at 964 cm$^{-1}$ is clearly visible on the spectra of all the immersed samples, and absent on that of the PDLLA control scaffold. To give some quantitative assessment based on these data, we calculated the ratio of the areas measured under the Band 1 phosphate peak and the C—COO peak at 873 cm$^{-1}$ for each spectrum (Table 5). A much higher ratio was measured on the treated than on the untreated scaffolds both after 2 and 4 weeks of immersion in SBF, thus confirming that a higher amount of HA was formed on the treated samples.

TABLE 5

Ratio of the areas measured on the Raman spectra under the phosphate-1 peak and the C—COO peak for untreated and P-PDLLA-2h-VT scaffolds after immersion in SBF for 2 and 4 weeks.

|  | Untreated | | P-PDLLA-2h-VT | |
| --- | --- | --- | --- | --- |
|  | 2 weeks | 4 weeks | 2 weeks | 4 weeks |
| $v_1$ (963 cm$^{-1}$)/ C—COO(873 cm$^{-1}$) | 0.089 | 0.168 | 0.125 | 0.241 |

In order to better understand the structure of the HA particles and their interaction with PDLLA, the inventors collected IR spectra on the particles extracted from the scaffolds.

Figure 12:
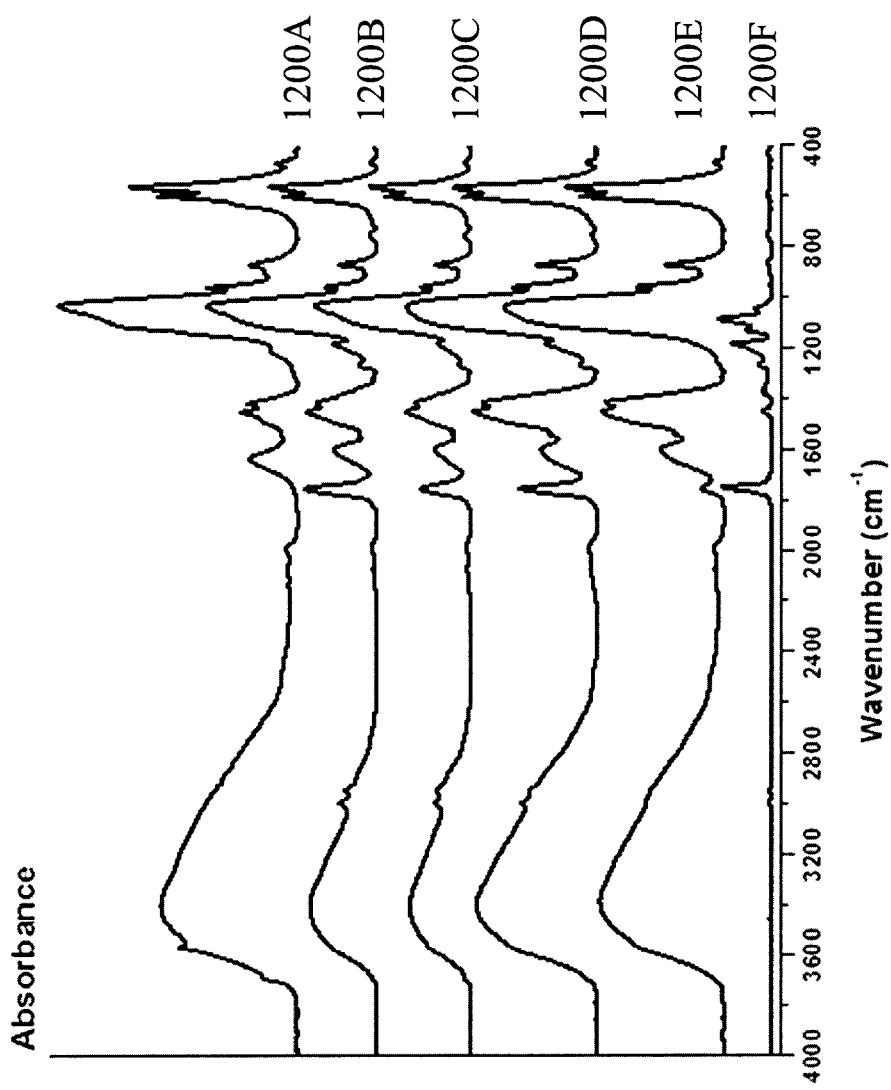
FIG. 12 depicts FT-IR spectra of untreated scaffolds after immersion in SBF together with treated P-PDLLA according to an embodiment of the invention after immersion in SBF together with PDLLA scaffold and HA control samples.

These are depicted in FIG. 12 with first to sixth traces 1200A to 1200F respectively wherein Second and fourth traces 1200B and 1200D respectively are FT-IR spectra of untreated scaffolds after 2 week and 4 week immersion in SBF;

Third and fifth traces 1200C and 1200E respectively are P-PDLLA-2h-VT scaffolds after 2 week and 4 week immersion in SBF;

Sixth trace 1200F is reference PDLLA scaffold; and

First trace 1200A is HA.

As evident in FIG. 12 all samples show the same peaks that are present in the spectrum of HA, and a few bands related to the polymer. The assignments of the peaks found on the spectra of the scaffolds after immersion in SBF related to HA and PDLLA are shown in Tables 6 and 7, respectively. The IR bands related to HA are present in the spectra of all the scaffolds and are in good agreement with data reported for several commercial HA powders. The only band that is present in the control HA powder but not on the powders extracted from the scaffolds is the one at approximately 3570 cm$^{-1}$, related to the structural isolated OH groups in HA. This absence may indicate a less ordered structured in the HA particles extracted from the scaffolds compared to the control HA. Also, all HA particles are carbonated as seen by the bands at around 1650 cm$^-$ and the one at 870 cm$^-$, more intense in the particles extracted from samples according to embodiments of the invention rather than in the HA control sample. The weak bands observed on the spectra of the particles extracted from the scaffolds at 2995 cm$^-$ and 2946 cm$^-$ and the stronger ones at 1756 cm$^{-1}$ and 1269 cm$^{-1}$ are related to the $v_{-CH3(ASYM)}$, and $v_{-CH3(SYM)}$, $v_{C=O}$, and $v_{C-O}$, respectively (Table 7). The presence of these bands indicates that some of the PDLLA from the scaffold matrix remained bound to the HA particles after their extraction. In fact, similar bands can be observed on the spectrum measured on pure PDLLA. The rest of the bands related to PDLLA fall in the same spectral region as the main peaks of HA, and thus cannot be observed. The presence of PDLLA peaks in the spectra of the extracted HA powders even after thorough acetone washes is remarkable, and suggests a strong (maybe covalent) interaction between the polymeric matrix and the HA particles nucleated on it.

TABLE 6

Assignments of the IR bands relative to HA, found on HA control and on the powders extracted from untreated and P-PDLLA-2h-VT scaffolds after immersion in SBF for 2 and 4 weeks (see FIG. 9).

| Peaks (cm$^{-1}$) | HA control | 2 weeks immersion in SBF | | 4 week immersion in SBF | |
| --- | --- | --- | --- | --- | --- |
|  |  | PDLLA | P-PDLLA-2h-VT | PDLLA | P-PDLLA-2h-VT |
| Hydroxyl stretch | 3568 | — | — | — | — |
| Carbonate $v_3$ -(m) | 1643 | 1602 | 1602 | 1602 | 1602 |
| -(m) |  | 1455 | 1452 | 1452 | 1452 | 1452 |
| -(m) |  | 1422 | 1423 | 1423 | 1422 | 1422 |
| Phosphate $v_3$ -(sh) | 1092 | 1088 | 1090 | 1087 | 1087 |
| -(vs) |  | 1034 | 1035 | 1035 | 1041 | 1041 |
| Phosphate $v_1$ | 962 | 961 | 961 | 960 | 960 |
| Carbonate $v_2$ | 875 | 873 | 873 | 874 | 874 |
| Phosphate $v_4$ -(s) | 601 | 603 | 603 | 602 | 602 |
| -(s) |  | 564 | 565 | 565 | 567 | 566 |
| Phosphate $v_2$ (w) | 472 | 469 | 471 | 470 | 470 |

TABLE 7

Assignments of the IR bands relative to PDLLA, found on PDLLA scaffold before immersion and on the powders extracted from untreated and P-PDLLA-2h-VT scaffolds after immersion in SBF for 2 and 4 weeks (see FIG. 9).

| Peaks (cm$^{-1}$) | Before immersion PDLLA scaffold | 2 weeks immersion in SBF | | 4 weeks immersion in SBF | |
| --- | --- | --- | --- | --- | --- |
|  |  | PDLLA | P-PDLLA-2h-VT | PDLLA | P-PDLLA-2h-VT |
| $v_{as}$ CH$_3$ | 2995 (m) | 2995 (m) | 2995 (m) | 2995 (m) | 2995 (m) |
| $v_s$ CH$_3$ | 2946 (m) | 2946 (m) | 2946 (m) | 2945 (m) | 2946 (m) |
| $v$ (C=O) | 1753 (vs) | 1756 (vs) | 1756 (vs) | 1756 (vs) | 1754 (vs) |
| $\delta_{as}$ CH$_3$ | 1452 | — | — | — | — |
| $\delta_s$ CH$_3$ | 1382 | — | — | — | — |
| $\delta_1$ CH + $\delta_s$ CH$_3$ | 1363 | — | — | — | — |
| $\delta$ CH + $v$ COC | 1269 | 1269 | 1269 | 1269 | 1269 |
| $v_{as}$ COC | 1186 (vs) | — | — | — | — |
| $r_{as}$ CH$_3$ | 1130 (s) | — | — | — | — |
| $v_s$ COC | 1088 (vs) | — | — | — | — |
| $v$ C—CH$_3$ | 1049 | — | — | — | — |
| R CH$_3$ + $v$CC | 957 (w) | — | — | — | — |

TABLE 7-continued

Assignments of the IR bands relative to PDLLA, found on PDLLA scaffold before immersion and on the powders extracted from untreated and P-PDLLA-2h-VT scaffolds after immersion in SBF for 2 and 4 weeks (see FIG. 9).

| Peaks (cm$^{-1}$) | Before immersion PDLLA scaffold | 2 weeks immersion in SBF | | 4 weeks immersion in SBF | |
|---|---|---|---|---|---|
| | | PDLLA | P-PDLLA-2h-VT | PDLLA | P-PDLLA-2h-VT |
| νCC—COO | 867 (s) | — | — | — | — |
| ν COO | 754 (w) | — | — | — | — |

In order to check the biocompatibility of the diazonium chemistry approach, the inventors prepared bi-dimensional films treated in the same way as the three-dimensional scaffolds, and examined the metabolic activities of chondrogenic ATDC5 and osteogenic MC3T3-E1 cells cultured on these films. The inventors tested three types of films: PDLLA films (PDLLA-f), films modified only with the first step of the diazonium treatment (FIG. 3C, N-PDLLA-f), and other films modified with all the steps (FIG. 3C, P-PDLLA-f).

Figures 13A, 13B:
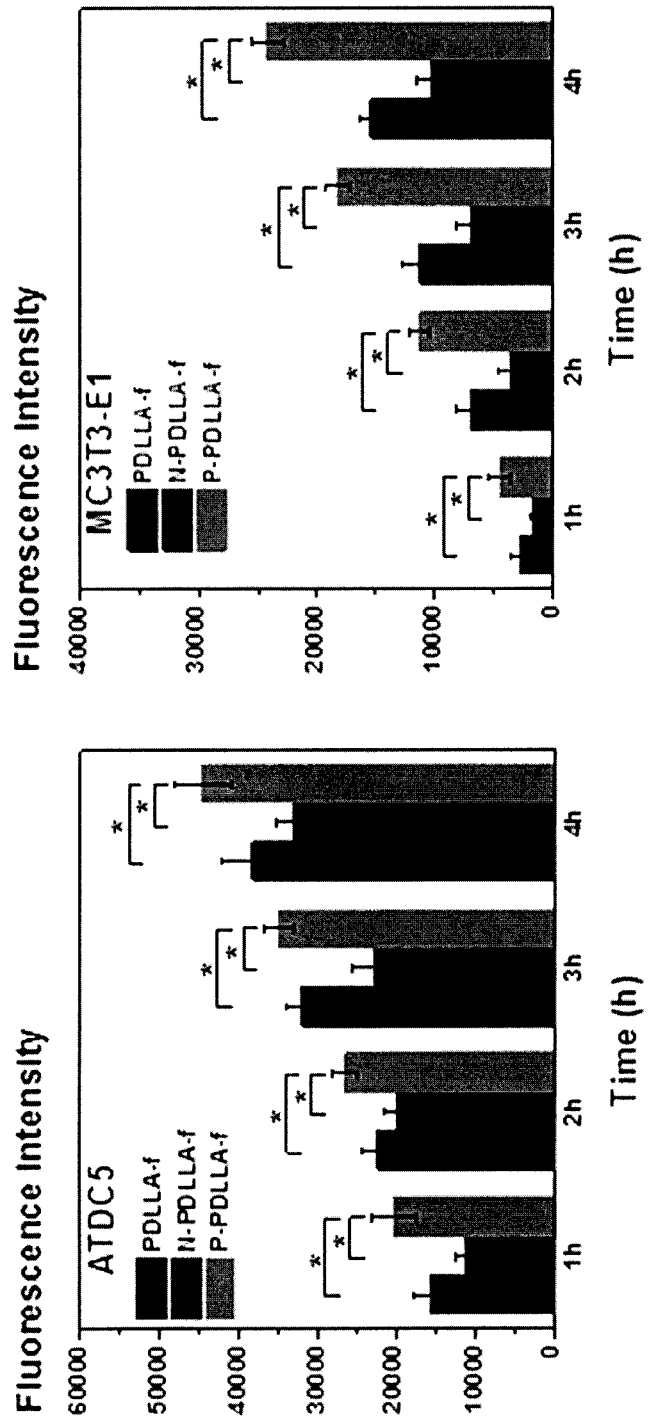
FIGS. 13A and 13B depict Alamar Blue assays of ATDC5 chondrogenic cells and MC3T3-E1 preosteoblasts seeded on PDLLA scaffolds according to embodiments of the invention.

Referring to FIGS. 13A and 13B there are metabolic activities of 4-day-old ATDC5 and MC3T3-E1 cultures as indicated by their ability of reduce Alamar Blue dye after 1, 2, 3 and 4 hours incubation at 37° C. The constant increase of Alamar blue reduction by the cells over a period of 4 hours shows that the cells are viable in all conditions. While cells grown on N-PDLLA-f show lower Alamar blue reduction compared to the control PDLLA-f, cells grown on the surface of P-PDLLA-f consistently show higher Alamar blue reduction than control PDLLA-f over all time periods. This shows that the introduction of phosphonate groups by diazonium chemistry enhanced the total cell metabolic activity, which can be caused by increased cell viability and/or proliferation.

Figure 14A:
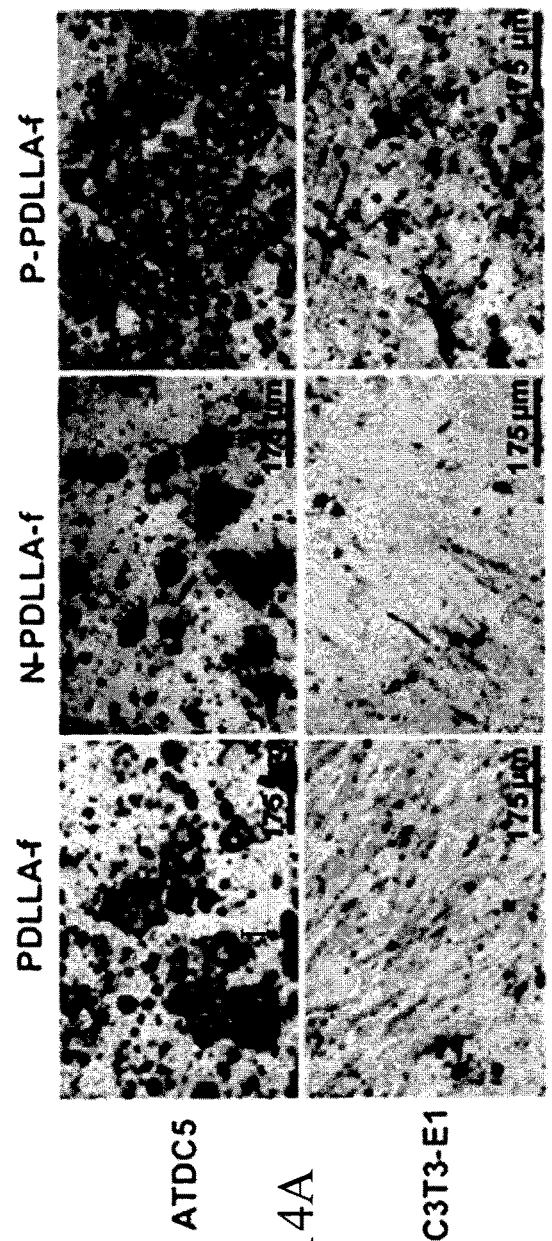
FIGS. 14A and 14B depict the Alizarin red staining and absorbance of alizarin dye for ATDC5 chondrogenic cells and MC3T3-E1 preosteoblasts seeded on PDLLA scaffolds according to embodiments of the invention.
Figure 14B:
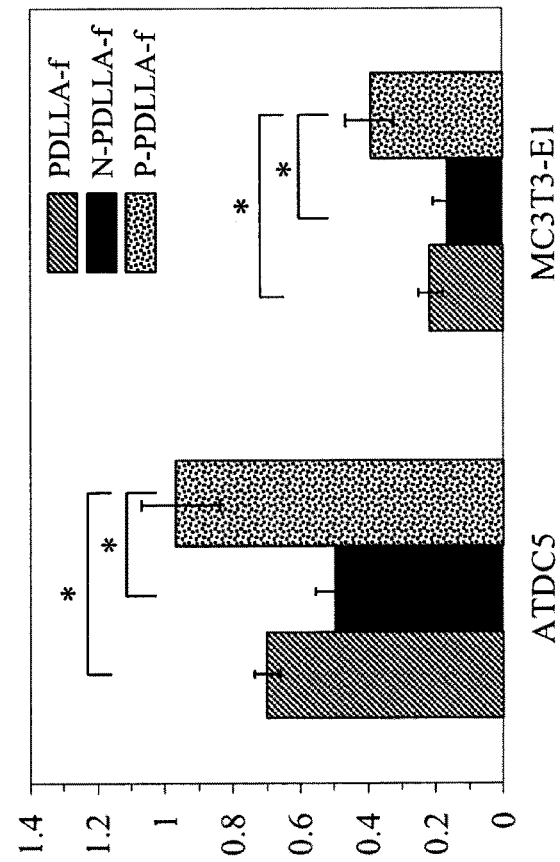

The in vitro mineralization ability of cultured osteogenic or chondrogenic cell lines is often used as a determinant of their functional properties. To investigate the effects of surface modification on the mineral deposition properties of ATDC5 and MC3T3-E1 cells, the inventors grew them in the presence of a differentiation medium (culture medium supplemented by ascorbic acid, -glycerol phosphate and dexamethasone) for 3 weeks. At the end of this period the cultures were stained by Alizarin red, a calcium binding dye. FIG. 14A shows that all the cultures grown on the surface of PDLLA-f, N-PDLLA-f and P-PDLLA-f deposited calcium-containing minerals. ATDC5 cells deposit more minerals than MC3T3-E1, which is to be related to intrinsic differences in mineral deposition properties between these two cell lines. The amount of bound Alizarin red is quantified in FIG. 14B. For both ATDC5 and MC3T3-E1 cultures, P-PDLLA-f films show the highest amount of mineral deposition among the three surfaces analyzed. This data is complementary to the observed increase in metabolic activities in the cultures grown on P-PDLLA-f and suggests that the phosphonate groups introduced via diazonium treatment enhanced the pro-mineralization properties of PDLLA.

Accordingly, the inventors have demonstrated a novel vacuum impregnation technique for modifying both the inner and outer surfaces of 3D PDLLA scaffolds for biomedical applications through a wet diazonium chemistry that does not degrade the underlying polymeric structure and allows the number of surface groups to be simply varied with a low cost chemistry methodology.

Further, the inventors have demonstrated that after binding aryldiazonium cations onto the scaffold surface they could successfully attach AEPA such that the phosphonate groups enhanced nucleation and growth of HA particles on the surfaces of PDLLA scaffolds. Accordingly, such surface modified scaffolds may be considered for orthopedic applications, since HA particles have excellent osteoconductivity and resorbability, and enhance bone growth and healing. However, the inventors also demonstrate that the diazonium treated surfaces were biocompatible on PDLLA surfaces both treated with the first step of the treatment (aminated) and after the subsequent modifications (phosphonated). Cells cultured on phosphonated PDLLA films showed higher metabolic activity and deposited more calcium-containing minerals than those cultured on bare PDLLA. Accordingly, coupling this with the fact that phosphonate groups are known to inhibit bone resorption it is possible to consider that phosphonate-functionalized scaffolds could be directly implanted, without necessarily pre-seeding them with HA.

The simplicity of this method, its biocompatibility and the fact that PDLLA is not degraded during the treatment makes it an ideal candidate to modify scaffolds for a variety of biomedical applications. In fact, after producing a "self-adhesive" layer rich in amino groups, many other groups can be easily bound to the scaffold, of which phosphonates represent just an example. One could use a similar method to bind peptides or proteins eliciting specific cellular functions, to make the scaffolds truly interactive with their surrounding tissues.

B: Polyether Ether Ketone (PEEK) Scaffolds

B1: Materials and Methods 1.5 mm thick PEEK films were either polished (PEEK-P) or roughened by sandblasting (PEEK-S) and phosphonated via diazonium chemistry. They are referred as PEEK-PT (polished and treated) and PEEK-ST (sandblasted and treated) after treatment within the ensuing description. In order to check confirm successful treatment XPS was performed on the surface of the samples. The wettability and mineralization of specimens were compared before and after treatment by sessile drop technique and 10 days of immersion in 1.5× concentrated SBF solution, respectively. The mineralized particles from SBF immersion test were analyzed by scanning electron microscopy (SEM), X-ray photoelectron spectroscopy (XPS), Fourier transform infrared spectroscopy (FT-IR) and a nanoscratch setup to investigate their morphology, mineral type and binding strength before and after treatment. The in vitro behaviour of these specimens was investigated by measuring the metabolic activity/viability and mineralization of MC3T3-E1 cells via Alamar Blue and Alizarin Red assays, respectively.

The procedure and mechanism for chemical grafting of phosphonate groups via diazonium chemistry onto polymeric surfaces has been previously described above in respect of PDLLA scaffolds in Section A. In common with that methodology and this work, $H_3PO_2$ was used as the reducing agent to generate stable aminophenyl radicals. Upon introduction of PEEK films into the aminophenyl radicals solution a multilayer structure of polyaminophenylene (PAP) was formed on their surfaces as depicted from FIG. 15A. In the next step in order to bind phosphonate containing groups (AEPA), the PAP layers were diazotized and transformed into polydiazophenylene layer (PDP) by the application of $NaNO_2$. The diazonium cations present on the PDP layer were reduced into radicals by $H_3PO_2$. This led to reaction between radicals and introduced AEPA in the solution and formation of a phosphonate-terminated multilayer structure as shown in FIG. 15B. Evidence of successful grafting of phosphonate groups on PEEK surfaces was provided by XPS. The relative atomic percentage of N and P acquired from XPS survey of samples is summarized in Table 8. There is no sign of N and P on PEEK-P and PEEK-S while presence of approximately 1.2%±0.4P and 3.4%±0.3N is confirmed for PEEK-PT and PEEK-ST. The consistency of results acquired from different points on the surface confirmed the homogeneity of grafted layer and reproducibility of the diazonium chemistry technique.

FIG. 15C depicts a high resolution spectrum of N1s for PEEK-PT. There is a peak at binding energy (BE) of 399.4 eV which belongs to amino groups grafted by diazonium chemistry due to reduction of aminophenyl groups. This peak contains a segment at 400 eV which corresponds to chemical structure of azo bridges (—N=N—) that are found in PDP layers and they are either the result of reaction between aminodiazenyl radicals or diazonium cations and radicals. The shoulder present at BE of 401.9 eV is related to the presence of ammonium (—$NH_3^+$) that has been previously reported to be present in diazonium grafted layers. The peak at BE of 406 eV corresponds to nitro groups but the mechanism of their formation is not clear. It could be due to usage of $NaNO_2$ in the grafting process or from solution contamination. The presence of P on PEEK-PT is confirmed by the P2P high resolution spectra (FIG. 15D). There is a peak at BE of 134.1 eV that belongs to phosphonate groups. The P2p peak at this binding energy was evident that in the previous results in Section A for the modification of PDLLA biodegradable scaffolds with phosphonate groups via diazonium chemistry.

immersion in 1.5×SBF solution. Presence of agglomerated particles on all samples is visible and the agglomerates observed on the surface of sandblasted samples (FIGS. 16C and 16D) were bigger and covered more surface area than polished samples (FIGS. 16A and 16B). Both PEEK-PT (FIG. 16B) and PEEK-ST (FIG. 16D) were covered more than the untreated ones but the amount of agglomerates on the PEEK-ST surfaces was significantly higher and the deposited particles completely covered the surface. The agglomerates present on all samples had sheet-like morphology that is previously observed for HA precipitation from SBF solutions [31, 45].

To quantify the immersion test results, the XPS survey spectra of immersion samples were analyzed (see Table 8). These results confirm the presence of Ca and P on the specimens after immersion testing. The Ca/P ratio measured on agglomerates was 1.6±0.1 suggesting formation of HA on all samples. The amount of Ca and P was higher on both PEEK-PT and PEEK-ST compared to their non-treated conditions due to presence of grafted phosphonate groups. Presence of grafted groups led to attraction of larger number of $Ca^{2+}$ cations, thus providing a higher number of HA nucleation sites and increasing the amount of precipitates. The effect of sandblasting was more dominant than the diazonium modification. The PEEK-S had higher amount of Ca and P compared to PEEK-P due to the rough morphology produced by sandblasting which provides more nucleation sites for HA precipitation. The diazonium treatment was able to increase the amount of precipitation for PEEK-PT and PEEK-ST at a reasonable amount and made the precipitate layer more homogenous. These results confirm that the amount of precipitation can be significantly increased by using sandblasting and diazonium treatment together.

TABLE 8

Summary of data acquired from specimens before and after diazonium treatment and SBF immersion test.

| | | | PEEK-P | PEEK-PT | PEEK-S | PEEK-ST |
|---|---|---|---|---|---|---|
| Diazonium modification | XPS | P (%) | 0.0 | 1.2 ± 0.3 | 0.0 | 1.1 ± 0.4 |
| | | N (%) | 0.0 | 3.5 ± 0.2 | 0.0 | 3.2 ± 0.4 |
| | Water contact angle | | 76.1° ± 1.1 | 67.2° ± 1.2 | 94.4° ± 0.8 | 82.2° ± 1.4 |
| SBF immersion test | XPS | Ca (%) | 2.4 ± 0.3 | 6.4 ± 0.7 | 17.1 ± 0.4 | 19.4 ± 0.9 |
| | | P (%) | 1.5 ± 0.2 | 3.9 ± 0.5 | 10.4 ± 0.3 | 11.8 ± 0.6 |
| | IR spectroscopy $v_3$ (1034 $cm^{-1}$)/DE (1227 $cm^{-1}$) | | 0.35 | 1.54 | 3.16 | 7.21 |
| HA binding strength | | | 15.5 ± 0.5 | 22 ± 3.5 | N/A | N/A |

A significant drawback of PEEK is its hydrophobic nature due to the low surface energy of the polymer. The inventors conducted water contact angle measurement on the surface of PEEK samples before and after treatment in order to understand the effects of sand blasting and diazonium chemistry modifications. The water contact angle value for each sample is shown in Table 8. Both PEEK-P and PEEK-S samples were less hydrophobic after diazonium treatment. The water contact angle of PEEK-PT decreased to 67.2°±1.2 from 76.1°±1.1 and the surface became less hydrophobic. Although the PEEK-S was more hydrophobic (94.4°±0.8) compared to PEEK-P due to its rougher surface the diazonium chemistry was able to decrease this value to 82.2°±1.4 and make it less hydrophobic.

To investigate if the functionalization was able to improve HA mineralization, the samples were immersed in 1.5×SBF solution for 10 days. FIGS. 16A to 16D depict SEM images taken from the surface of specimens after 10 days of The inventors conducted FT-IR spectroscopy on the surface of samples in order to confirm that the precipitates were HA. All of the immersed samples show the same peaks present in the control PEEK and in the HA spectrum. There were peaks present at 1034 $cm^{-1}$ with a shoulder at 1087 $cm^{-1}$ and a small peak at 963 $cm^{-1}$ which are in good agreement with the data reported for $v_3$ and $v_1$ phosphate band of HA powder, respectively as noted supra in respect of Section A. To have a more quantitative analysis of these data, the ratio of the area under the $v_3$ phosphate band at 1043 $cm^{-1}$ to asymmetric stretching of diphenyl ether (DE) groups at 1227 $cm^{-1}$ was calculated. The PEEK-ST samples had the highest ratio among all conditions which confirms they higher amount of HA precipitates (see Table 8).

Figure 17B:
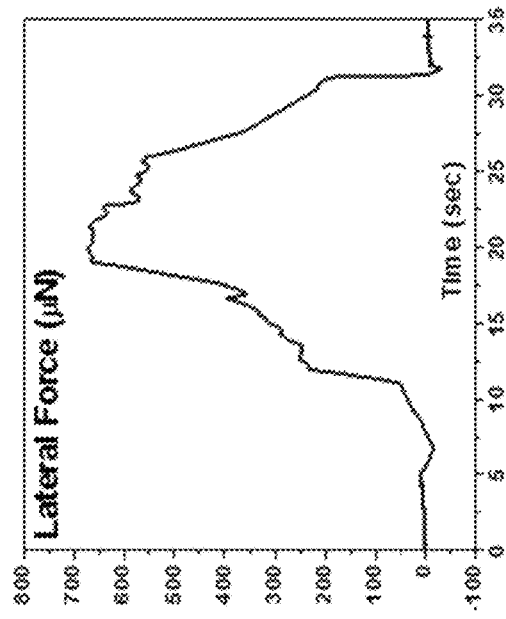
FIGS. 17A to 17D depict a nano-scratch test setup together with lateral force versus time recorded during particle displacement and SPM images of an HA particle before and after scratch testing of PEEK-PT prepared according to an embodiment of the invention.
Figure 17A:
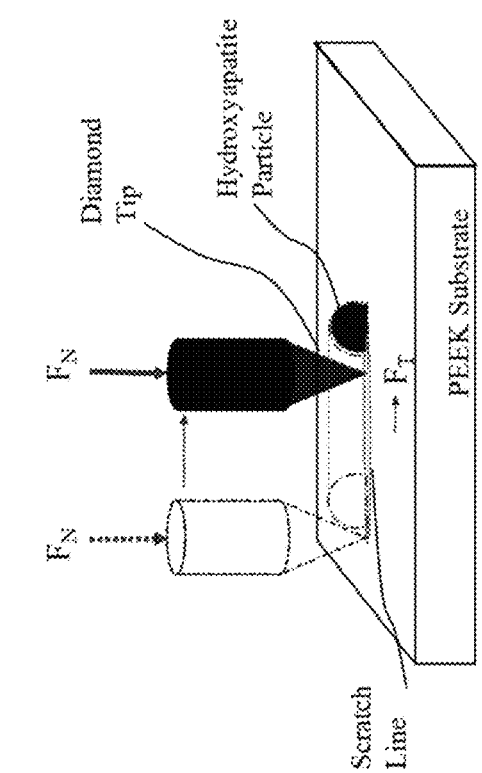
Figure 17D:
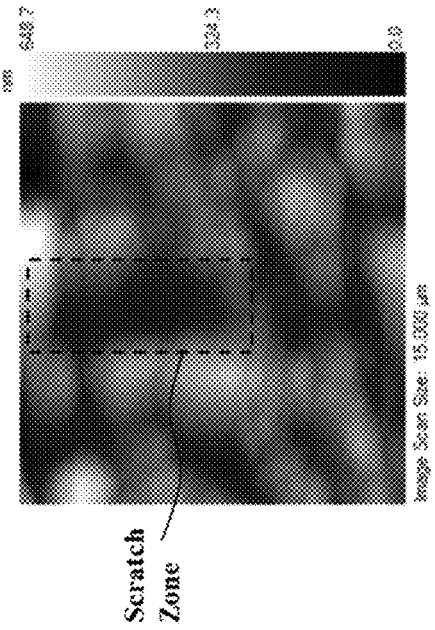
Figure 17C:
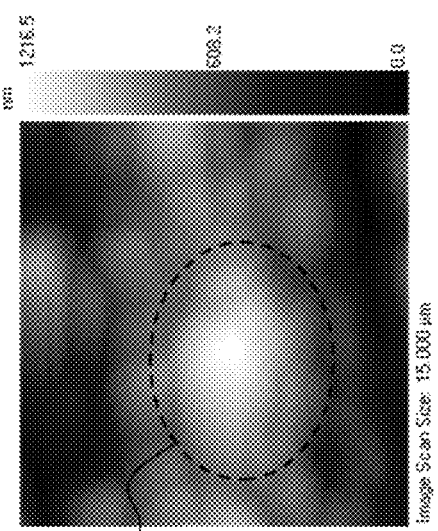

To understand the adhesion strength of 1034 $cm^{-1}$ particles a nanoscratch test was conducted. A normal load of 1 mN was applied to the substrate and the diamond tip was moved 10 μm laterally and during the process the tip displaced the 1034 cm$^{-1}$ particle adhered to PEEK-ST surface as depicted in FIG. 17A. SPM images were recorded to identify the particle position before (FIG. 17C) and after (FIG. 17D) the scratch test. The lateral force experienced by the indenter during the process of particle displacement was used to calculate the adhesion strength (FIG. 17B).

Figure 18B:
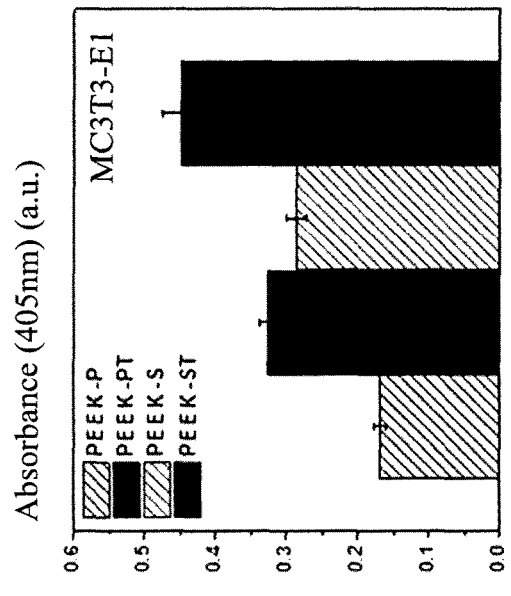
FIGS. 18A and 18B depicts Alamar Blue and Alizarin red assays of MC3T3-E1 preosteoblast cells seeded on PEEK surfaces prepared according to embodiments of the invention after 1 week and 1 month.
Figure 18A:
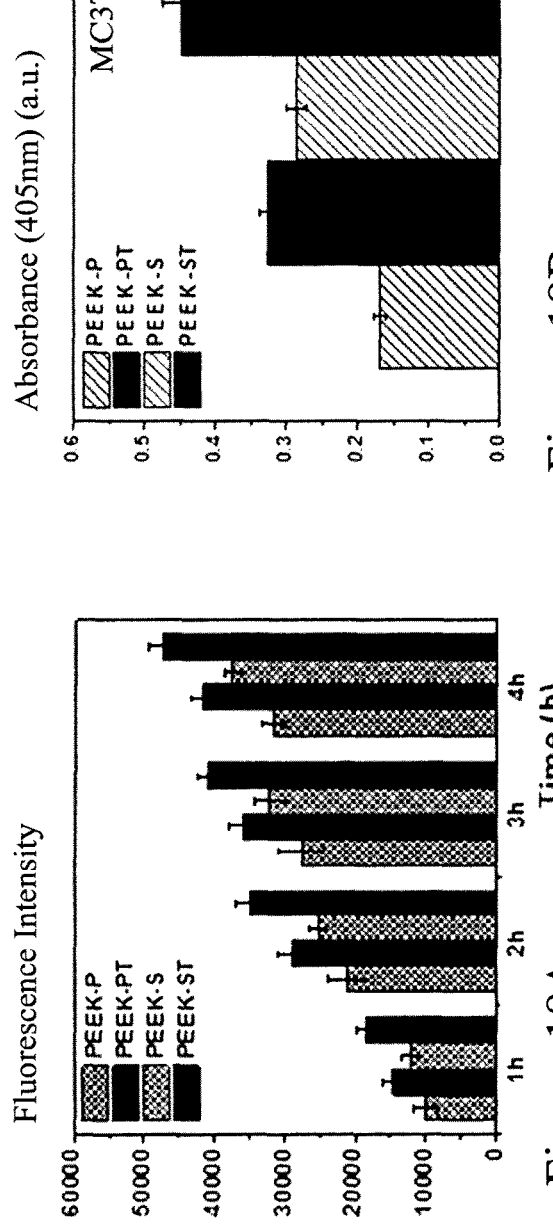

To investigate the effect of sand blasting and diazonium treatment on biocompatibility of PEEK samples, metabolic activity of osteogenic MC3T3-E1 cells cultured on all conditions and thin discs were examined. The metabolic activity of 7-day-old cultures was measured fluorometrically after 1, 2, 3 and 4 hours incubation at 37° C. as depicted in FIG. 18A. All samples showed an increase of dye reduction by cells over time which confirms viability of all conditions. The sandblasted PEEK showed higher metabolic activity/viability compared to the polished sample due to the availability of more anchorage sites provided by sandblasting. But the treated polished sample had higher dye reduction than just sandblasted PEEK sample which suggests that the effect of diazonium chemistry is more important than sandblasting. Finally, the highest amount of reduction of Alamar blue dye is in treated sandblasted PEEK samples. This confirms that sandblasting and presence of the grafted phosphonate groups by diazonium chemistry together increased the total cell metabolic activity compare to each condition alone.

The biomineralization of bone cells play an important role in healing process of bone tissue, thus the effect of diazonium treatment and sandblasting on the in vitro mineral deposition properties of MC3T3-E1 cells were investigated. The inventors grew the cells in differentiation medium containing ascorbic acid, β-glycerol phosphate, and dexamethasone for a period of 1 month. The samples were stained with Alizarin red dye that binds to the calcium containing mineral deposits. FIG. 18B demonstrates the amount of deposited calcium-containing minerals on different PEEK surfaces after 1 month. The treated polished samples show slightly higher amount of mineral deposition compared to sandblasted ones which suggest that effect of diazonium modification is greater than sandblasting. But the combined effect of chemical diazonium treatment and physical sandblasting was best and led to deposition of higher amount of mineral deposits on the surface of treated sandblasted PEEK samples.

Accordingly, the inventors have demonstrated that the combination of two simple modification techniques, diazonium chemistry and roughening (in this instance via sandblasting), allow the PEEK polymer surface to be modified homogenously and phosphonate groups grafted to it in order to increase the nucleation and growth of HA particles on the surface of PEEK samples after immersion in concentrated SBF solution. The inventors were further able to demonstrate that HA particles precipitated on diazonium treated surfaces had higher binding strength compared to non-treated samples suggesting that the modification is able to enhance production of HA-coated scaffolds with higher HA adhesion strength which leads to less manufacturing issues of such scaffolds. Further, in vitro tests confirmed that the highest metabolic activity and most calcium-containing deposits compare were achieved by combining roughening and diazonium modification. The combination of these two simple techniques is able to produce scaffolds that can be directly implanted without pre-HA coating. It also can enhance the precipitation process of HA particles with high binding strength on the surface of scaffolds prior to implantation. This method is very cost effective compare to available HA spray coating methods, does not suffer from line of sight issue and is able to modify complex structures. Furthermore, many other chemical groups, peptides or proteins can be grafted to the surface with diazonium chemistry and can improve the response of PEEK scaffold to the other tissues than bone.

C. Poly(Methyl Methacrylate) (PMMA) Scaffolds

In order to demonstrate the established diazonium chemistry upon another polymeric material the inventors processed PMMA Petri dishes using the diazonium chemistry established and described above in respect of Sections A and B after which they were exposed 2-aminoethylphosphonic acid (AEPA) for varying periods of time as listed below in Table 9.

Upon introduction of the PMMA dishes a multilayer structure of polyaminophenylene (PAP) is formed on their surfaces, diazotided and transformed into polydiazophenylene layer (PDP) by the application of $NaNO_2$ as discussed supra. The diazonium cations present on the PDP layer are reduced into radicals by $H_3PO_2$ as discussed supra. This leads to reaction between radicals and introduced AEPA in the solution and formation of a phosphonate-terminated multilayer structure.

Figure 19:
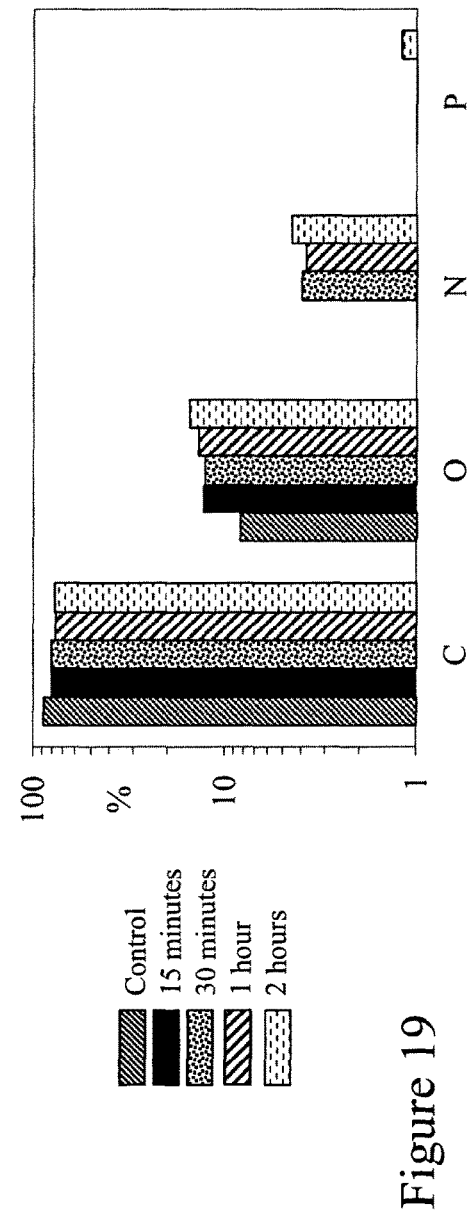
FIG. 19 depicts XPS for PMMA samples showing that N and P are only present after processing according to embodiments of the invention with AEPA as the reacting molecule.

The PMMA Petri dishes were then dried and analyzed with XPS yielding the results presented in Table 9 and depicted in FIG. 19. As evident the results are consistent with those for PDLLA and PEEK XPS wherein the N and P atoms present on the PMMA surface is proportional to the time of exposure to the reaction solutions.

TABLE 9

XPS data showing N and P formed on poly-methyl methacrylate (PMMA) samples after 2-step process with AEPA as reacting molecule.

| | C | O | N | P | Si + Cl |
|---|---|---|---|---|---|
| Control | 87.7 ± 3.1 | 8.3 ± 2.3 | — | — | Balance |
| 15 min | 80.7 ± 2.6 | 13.2 ± 1.7 | 0.27 ± 2.3 | 0.27 ± 0.3 | Balance |
| 30 min | 79.9 ± 2.2 | 12.6 ± 1.1 | 4.0 ± 2.6 | 0.3 ± 0.26 | Balance |
| 1 h | 76.0 ± 0.8 | 13.8 ± 0.9 | 3.8 ± 1.2 | 0.6 ± 0.1 | Balance |
| 2 h | 77.3 ± 1.6 | 15.3 ± 1.2 | 4.5 ± 0.5 | 1.2 ± 0.2 | Balance |

D. One-Step Process Surface Modification for Scaffolds

Within the preceding Sections A and B in respect of diazonium chemistry for the modification of polyester (PDLLA) and thermoplastic (PEEK, PMMA) material surfaces the processing sequence comprised:
  (A) establishing a multilayer structure, which was achieved with the following steps:
    (i) formation of aminophenyl monosubstituted diazonium cations;
    (ii) reducing the aminophenyl monosubstituted diazonium cations to aminophenyl radicals; and
    (iii) establishing a multilayer structure by exposing the scaffold/material to the aminophenyl radicals; and
  (B) diazotizing the multilayer structure to form a multilayer terminated with a predetermined chemical grouping.

The inventors refer to this as a two-stage process. As discussed supra embodiments of the invention may include the addition of a vacuum/low pressure stage in order to ensure appropriate penetration of the two-stage process into pores/holes/etc. within the material being treated and/or the addition of a surface roughening stage. However, it would be beneficial to provide a single stage process further reducing the complexity of the modifications made to the materials inner and/or outer surfaces.

Accordingly, the inventors have established a one-stage process of which an embodiment of the invention comprises the steps of:
Exposing a sample to a solution of 4-aminobenzylphosphonic acid dissolved in 0.5 M HCl or $H_2SO_4$;
Adding $NaNO_2$ and $H_3PO_2$ and allowing the reaction to proceed for a predetermined period of time (for example 24 hours).

Within the preceding descriptions in respect of Sections A to D PDLLA, PEEK, and PMMA scaffolds have been described with respect to the two-stage vacuum-diazonium chemistry processing. It would be evident that other polymers may be employed without departing from the scope of the invention. Further, scaffolds such as described and enhanced by said two-stage vacuum-diazonium chemistry processing may be used for human implants as well as animal implants.

Beneficially the diazonium chemistry processes employed by the inventors exploit in-situ formation of diazonium cations in contact with the surface. According, for example, the inventors start with dianiline and reduce it in-situ chemically. This is advantageous as dianiline is commercially available, relatively inexpensively compared to diazonium salts and is completely stable so it is easier to control its reactivity. Further, the inventors then react the amino-terminated layer with aminoethyl phosphonic acid which is important for applications such as hydroxyapatite (HA) deposition on polymeric scaffolds but also for the improvement of cell adhesion and proliferation on polymeric scaffolds. Additionally, vacuum processing provides inner and outer surface modifications and in some instances roughening further enhances the processes. Scaffolds established according to the processes of the inventors may, in principle, be employed directly with phosphonate groups or after HA deposition via immersion in simulated body fluid after diazonium modification.

Within the preceding specification, the use of physical surface modification was described with respect to exemplary embodiment(s) only, and is not intended to limit the scope, applicability or configuration of the disclosure. Accordingly, whilst the description and applications with respect to the exemplary embodiments using PEEK sandblasting was described it would be evident that this technique may also be applied to other materials such as other thermoplastics, polyesters, metals, and glasses. However, it would also be evident that other processes with or without line-of-sight requirements/restrictions including, but not limited to, laser ablation, laser surface profiling, etching, molding, and stamping may be employed.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of treating a scaffold comprising
modifying at least one of an inner and an outer surfaces of the scaffold using a diazonium chemistry process to covalently graft at least one functional group on the at least one of the inner and outer surfaces,
wherein the diazonium chemistry process comprises the formation of at least one reactive radical, and
wherein the diazonium chemistry process is performed under vacuum conditions.

2. The method according to claim 1, wherein the modifying step comprises:
a) forming a first diazonium cation;
b) reducing the first diazonium cation into a first reactive radical;
c) contacting the first reactive radical with the at least one of the inner and outer surfaces to form a first multilayer structure; and
d) optionally diazotizing the first multilayer structure to form a second diazonium cation and a second reactive radical to react with a binding agent and form a second multilayer structure,
wherein the functional group is present:
on the first diazonium cation so that the first multilayer structure is terminated with the at least one functional group, or
optionally on the binding agent so that the second multilayer structure is terminated with the at least one functional group.

3. The method according to claim 2, wherein the first and the second diazonium cations are substituted aminophenyl cations and the first and second reactive radicals are substituted aminophenyl radicals.

4. The method according to claim 3, wherein
step (a) comprises the reduction of 4-aminobenzylphosphonic acid or p-phenylenediamine;
step (b) is performed using $NaNO_2$ and $H_3PO_2$ as reducing agents; and
optionally, step (d) is performed using 2-aminoethylphosphonic acid (AEPA) as the binding agent, and $NaNO_2$ and $H_3PO_2$ as reducing agents.

5. The method according to claim 4, wherein steps a) to d) are performed in situ with the scaffold.

6. The method according to claim 1, wherein the at least one functional group is one of a chemical group, a redox species, a dendrimers, a peptide, and a protein.

7. The method according to claim 6, wherein the chemical group is a phosponate.

8. The method according to claim 1, further comprising, prior to the modifying step, roughening at least one of the inner and outer surfaces of the scaffold.

9. A scaffold having an inner and an outer surface, wherein at least one of the inner and outer surfaces is covalently grafted with at least one functional group and has been modified using a diazonium chemistry process, wherein the diazonium chemistry process comprises the formation of at least one reactive radical, and wherein the at least one of the inner and outer surfaces of the scaffold has been modified under vacuum conditions.

10. The scaffold of claim 9, wherein the at least one of the inner and outer surfaces has been modified by performing the following steps:

a) forming a first diazonium cation;

b) reducing the first diazonium cation into a first reactive radical;

c) contacting the first reactive radical with the at least one of the inner and outer surfaces to form a first multilayer structure; and d) optionally diazotizing the first multilayer structure to form a second diazonium cation and a second reactive radical to react with a binding agent and form a second multilayer structure, wherein the functional group is on the first diazonium cation and is covalently grafted on the first multilayer structure, or optionally on the binding agent and is covalently grafted on the second multilayer structure.

11. The scaffold according to claim 10, wherein the first and the second diazonium cations are substituted aminophenyl cations and the first and second reactive radicals are substituted aminophenyl radicals.

12. The scaffold according to claim 11, wherein step (a) comprises the reduction of 4-aminobenzylphosphonic acid or p-phenylenediamine;

step (b) is performed using $NaNO_2$ and $H_3PO_2$ as reducing agents; and optionally, step (d) is performed using 2-aminoethylphosphonic acid (AEPA) as the binding agent, and $NaNO_2$ and $H_3PO_2$ as reducing agents.

13. The scaffold according to claim 9, wherein the at least one functional group is one of a chemical group, a redox species, a dendrimer, a peptide, and a protein.

14. The scaffold according to claim 13, wherein the chemical group is a phosphonate.

15. The scaffold according to claim 9, wherein the at least one of the inner and outer surfaces has been pre-treated using a roughening process, prior to the modifying step.

16. The scaffold according to claim 9, wherein the scaffold is a biomedical implant for an animal, a biomedical implant for a human, a predetermined portion of a culturing system, or a bead, wherein the at least one functional group is selected for interaction with surrounding tissue of the corresponding animal, human, culturing system or bead.

17. A method for implanting a scaffold as defined in claim 9, wherein the scaffold is implanted without at least one of biomineralization and hydroxyapatite deposition.

* * * * *